(12) United States Patent
Kim et al.

(10) Patent No.: US 7,153,949 B2
(45) Date of Patent: Dec. 26, 2006

(54) NUCLEIC ACID ENCODING POLY-ZINC FINGER PROTEINS WITH IMPROVED LINKERS

(75) Inventors: Jin-Soo Kim, Inchon (KR); Carl O. Pabo, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 50 days.

(21) Appl. No.: 11/110,594

(22) Filed: Apr. 20, 2005

(65) Prior Publication Data

US 2005/0202498 A1 Sep. 15, 2005

Related U.S. Application Data

(63) Continuation of application No. 10/146,221, filed on May 13, 2002, now Pat. No. 6,903,185, which is a continuation of application No. 09/260,629, filed on Mar. 1, 1999, now Pat. No. 6,479,626.

(60) Provisional application No. 60/076,454, filed on Mar. 2, 1998.

(51) Int. Cl.
*C07H 21/02* (2006.01)
*C07K 14/00* (2006.01)

(52) U.S. Cl. ..................... 536/23.1; 530/350
(58) Field of Classification Search ............... 536/23.1; 530/350
See application file for complete search history.

(56) References Cited

U.S. PATENT DOCUMENTS

| | | |
|---|---|---|
| 4,990,607 A | 2/1991 | Katagiri et al. |
| 5,096,814 A | 3/1992 | Aivasidis et al. |
| 5,096,815 A | 3/1992 | Ladner et al. |
| 5,198,346 A | 3/1993 | Ladner et al. |
| 5,223,409 A | 6/1993 | Ladner et al. |
| 5,243,041 A | 9/1993 | Fernandez-Pol |
| 5,302,519 A | 4/1994 | Blackwood et al. |
| 5,324,638 A | 6/1994 | Tao et al. |
| 5,324,818 A | 6/1994 | Nabel et al. |
| 5,324,819 A | 6/1994 | Oppermann et al. |
| 5,340,739 A | 8/1994 | Stevens et al. |
| 5,348,864 A | 9/1994 | Barbacid |
| 5,350,840 A | 9/1994 | Call et al. |
| 5,356,802 A | 10/1994 | Chandrasegaran |
| 5,376,530 A | 12/1994 | De The et al. |
| 5,403,484 A | 4/1995 | Ladner et al. |
| 5,436,150 A | 7/1995 | Chandrasegaran |
| 5,487,994 A | 1/1996 | Chandrasegaran |
| 5,498,530 A | 3/1996 | Schatz et al. |
| 5,578,483 A | 11/1996 | Evans et al. |
| 5,597,693 A | 1/1997 | Evans et al. |
| 5,639,592 A | 6/1997 | Evans et al. |
| 5,674,738 A | 10/1997 | Abramson et al. |
| 5,702,914 A | 12/1997 | Evans et al. |
| 5,789,538 A | 8/1998 | Rebar et al. |
| 5,792,640 A | 8/1998 | Chandrasegaran |
| 5,869,618 A | 2/1999 | Lippman et al. |
| 5,871,902 A | 2/1999 | Weininger et al. |
| 5,871,907 A | 2/1999 | Winter et al. |
| 5,916,794 A | 6/1999 | Chandrasegaran |
| 5,939,538 A | 8/1999 | Leavitt et al. |
| 5,972,615 A | 10/1999 | An et al. |
| 6,001,885 A | 12/1999 | Vega et al. |
| 6,007,988 A | 12/1999 | Choo et al. |
| 6,013,453 A | 1/2000 | Choo et al. |
| 6,110,747 A | 8/2000 | Blaschuk et al. |
| 6,140,466 A | 10/2000 | Barbas, III et al. |
| 6,479,626 B1 * | 11/2002 | Kim et al. .................. 530/300 |
| 6,534,261 B1 | 3/2003 | Cox, III et al. |
| 6,903,185 B1 * | 6/2005 | Kim et al. .................. 530/300 |
| 2002/0173006 A1 * | 11/2002 | Kim et al. ................. 435/69.1 |

FOREIGN PATENT DOCUMENTS

| | | |
|---|---|---|
| EP | 0 875 567 A2 | 11/1998 |
| WO | WO 95/19431 | 7/1995 |
| WO | WO 96/06110 | 2/1996 |
| WO | WO 96/06166 | 2/1996 |
| WO | WO 96/11267 | 4/1996 |
| WO | WO 96/20951 | 7/1996 |
| WO | WO 96/32475 | 10/1996 |
| WO | WO 97/27212 | 7/1997 |
| WO | WO 97/27213 | 7/1997 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 99/36553 | 7/1999 |
| WO | WO 99/41371 | 8/1999 |

(Continued)

OTHER PUBLICATIONS

Agarwal et al., "Stimulation of Transcript Elongation Requires Both the Zinc Finger and RNA Polymerase II Binding Domains of Human TFIIS," *Biochemistry* 30(31):7842-7851 (1991).

(Continued)

*Primary Examiner*—Karen Cochrane Carlson
(74) *Attorney, Agent, or Firm*—Robins & Pasternak LLP; Sean M. Brennan

(57) ABSTRACT

Polynucleotides encoding chimeric proteins, and methods for their production and use are disclosed. The chimeric proteins comprise a flexible linker between two zinc finger DNA-binding domains, wherein the linker contains eight or more amino acids between the second conserved histidine residue of the carboxy-terminal zinc finger of the first domain and the first conserved cysteine residue of the amino-terminal zinc finger of the second domain.

30 Claims, 5 Drawing Sheets

FOREIGN PATENT DOCUMENTS

| | | |
|---|---|---|
| WO | WO 99/42474 | 8/1999 |
| WO | WO 99/45132 | 9/1999 |
| WO | WO 99/47656 | 9/1999 |
| WO | WO 99/48909 | 9/1999 |
| WO | WO 00/23464 | 4/2000 |
| WO | WO 00/27878 | 5/2000 |
| WO | WO 01/53480 A1 | 7/2001 |

OTHER PUBLICATIONS

Antao et al., "A Thermodynamic Study of Unusually Stable RNA and DNA Hairpins," *Nuc. Acids. Res.* 19(21):5901:5905 (1991).

Barbas, C.F., "Recent Advances in Phage Display," *Curr. Opin. Biotech.* 4:526-530 (1993).

Barbas et al., "Assembly of Combinatoria Antibody Libraries on Phage Surfaces: The Gene III Site," *PNAS* 88:7978-7982 (1991).

Barbas et al., "Semisynthetic Combinatorial Antibody Libraries: A Chemical Solution to the Diversity Problem," *PNAS* 89:4457-4461 (1992).

Beerli et al., "Toward Controlling Gene Expression at Will: Specific Regulation of the erbB-2/HER-2 Promoter by Using Polydactyl Zinc Finger Proteins Constructed From Modular Building Blocks," *Proc. Natl. Acad. Sci. U.S.A.* 95:14628-14633 (1998).

Bellefroid et al., "Clustered Organization of Homologous KRAB Zinc-Finger Genes with Enhanced Expression in Human T Lymphoid Cells," *EMBO J.* 12(4):1363-1374 (1993).

Berg, J.M., "DNA Binding Specificity of Steriod Receptors," *Cell* 57:1065-1068 (1989).

Berg, J.M., "Sp1 and the Subfamily of Zinc-Finger Proteins with Guanine-Rich Binding Sites," *PNAS* 89:11109-11110 (1992).

Berg, J.M., "The Galvanization of Biology: A Growing Appreciation for the Roles of Zinc" *Science* 271:1081-1085 (1996).

Berg, J.M., "Letting Your Fingers do the Walking," *Nature Biotechnology* 15:323 (1997).

Bergqvist et al., "Loss of DNA-binding and new Transcriptional Trans-Activation Function in Polyomavirus Large T-Antigen with Mutation of Zinc Finger Motif," *Nuc. Acids Res.* 18(19):2715-2720 (1990).

Blaese et al., "Vectors in Cancer Therapy: How Will They Deliver?," *Cancer Gene Therapy* 2(4):291-297 (1995).

Caponigro et al, "Trasdominant Genetic Analysis of a Growth Control Pathway," *PNAS* 95:7508-7513 (1998).

Celenza et al., "A Yeast Gene That is Essential for Release from Glucose Repression Encodes a Protein Kinase" *Science* 233:1175-1180 (1996).

Cheng et al., "Identification of Potential Target Genes for Adrip Through Characterization of Essential Nucleotides in UASI," *Mol. Cellular Biol.* 14(6):3842-3852 (1994).

Cheng et al., "A Single Amino Acid Substitution in Zinc Finger 2 of Adrip Changes its Binding Specificity at two Positions in UAS1," *J. Mol. Biol.* 251:1-8 (1995).

Choo et al., A Role in DNA-Binding for the Linker Sequences of the First Three Zinc Fingers of TFIIIA *Nuc. Acids Res.* 21(15):3341-3346 (1993).

Choo et al., "Promoter-Specific Activation of Gene Expression Directed by Bacteriophage-Selected Zinc Fingers," *J. Mol. Biol.* 273:525-532 (1997).

Choo et al., "Designing DNA-Binding Proteins on the Surface of Filamentous Phage," *Curr. Opin. Biotechnology* 6:431-436 (1995).

Choo, Y., "Recognition of DNA Methylation by Zinc Fingers," *Nature Struct Biol*, 5(4):264-265 (1998).

Choo et al., "All Wrapped Up," *Nature Struct Biol* 5(4):253-255 (1998).

Choo, Y., "End Effects in DNA Recognition Code," *Nuc. Acids. Res.* 26(2):554-557 (1998).

Choo et al., Physical Basis of Protein-DNA Recognition Code, *Curr. Opin. Struct. Biol.* 7(1):117-125 (1997).

Choo et al., "Toward a Code for the Interactions of Zinc Fingers With DNA: Selection of Randomized Fingers Displayed on Phage," *Proc. Natl. Acad. Sci. U.S.A.* 91:11163-11167 (1994).

Choo et al., "Selection of DNA Binding Sites for Zinc Fingers using Randomized DNAs reveals Coded Interactions," *Proc. Natl. Acad. Sci. U.S.A.* 91:11168-11172 (1994).

Choo et al., "*In vivo* Repressuin by a Site-Specific DNA-Binding Protein Designed against an Onogenic Sequence," *Nature* 372:642-645 (1994).

Clarke et al., "Zinc Fingers in *Caenorhabditis elegans*: Finding Families and Probing Pathways," *Science* 282:2018-2022 (1998).

Clemens et al., "Relative contributions of the zinc fingers of transcription factor IIIA to the energetics of DNA binding," *J. Molecular Biology* 244(1):23-35 (1994).

Crobi et al., "Synthesis of a New Zinc Finger Peptide: Comparison of Its "Code" Deduced and "CASTing" Derived Binding Sites," *FEBS Letters* 417:71-74 (1997).

Crozatier et al., "Single Amino Acid Exchanges in Separate Domains of the Drosophila Serendipity Zinc Finger Protein Cause Embroyonic and Sex Biased Lethality," *Genetics* 131:905-916 (1992).

Debs et al., "Regulation of Gene Expression in Vivo by Liposome-Mediated Delivery of a Purified Transcription Factor," *J. Biological Chemistry* 265(18):10189-10192 (1990).

Desjarlais et al., "Redesigning the DNA-Binding Specificity of a Zinc Finger Protein: A Data Base-Guided Approach," *Proteins: Structure, Function, and Genetics* 12(2):101-104 (1992).

Desjarlais et al., "Redesigning the DNA-Binding Specificity of a Zinc Finger Protein: A Data Base-Guided Approach," *Sturcture, Function, and Genetics* 13(3):272 (1992).

Desjarlais et al., "Toward Rules Relating Zinc Finger Protein Sequences and DNA Binding Site Perferences," *PNAS* 89:7345-7349 (1992).

Desjarlais et al., "Use of a Zinc-Finger Consensus Sequence Framework and Specificity Rules to Design Specific DNA Binding, Proteins," *PNAS* 90:2256-2260 (1993).

Desjarlais et al., "Length-Encoded Multiplex binding Site Determination: Application to Zinc Finger Proteins," *PNAS* 91:11099-11103 (1994).

Dibello et al., "The Drosophila *Broad-Complex* Encodes a Family of Related Proteins Containing Zinc Fingers," *Genetics* 129:385-397 (1991).

Elrod-Erickson et al., "High Resolution Structures of Variant Zif268-DNA Complexes: Implications for Understanding Zinc Finger-DNA Recognition," *Structure* 6(4):451-464 (1998).

Elrod-Erickson et al., "Zif268 Protein-DNA Complex Refined at 1.6 Å: a Model System for Understanding Zinc Finger-DNA Interactions," *Structure* 4(10):1171-1180 (1996).

Fairall et al., "The Crystal Structure of a Two Zinc-Finger Peptide Reveals an Extension to the Rules for Zinc-Finger /DNA Recognition," *Nature* 366:483-487 (1993).

Frankel et al., "Fingering Too Many Proteins," *Cell* 53:675 (1988).

Friesen et al., "Phage Display of RNA Binding Zinc Fingers from Transcription Factor IIA," *J. Biological Chem.* 272(17):10994-10997 (1997).

Friesen et al., "Specific RNA Binding Proteins Constructed from Zinc Fingers," *Nature Structural Biology* 5(7):543-546 (1998).

Gogos et al., "Recognition of Diverse Sequences by Class I Zinc Fingers: Asymmetries and Indirect Effects on Specificity in the Interaction Between CF2II and A+T-Rich Sequences Elements," *PNAS* 93(5):2159-2164 (1996).

Gossen et al., "Tight Control of Gene Expression in Mammalian Cells by Tetracycline-Responsive Promoter," *PNAS* 89:5547-5551 (1992).

Greisman & Pabo, "A General Strategy for Selecting High-Affinity Zinc Finger Proteins for Diverse DNA Target Sites" *Science* 275:657-661 (1997).

Hamilton et al., "High Affinity Binding Sites for the Wilms' Tumor Suppressor Protein WTI," *Nuc. Acids. Res.* 23(2):277-284 (1995).

Hamilton et al., "Comparison of the DNA Binding Characteristics of the Related Zinc Finger Proteins WT1 and EGR1," *Biochemistry* 37:2051-2058 (1998).

Hanas et al., "Internal Deletion Mutants of *Xenopus* Transcription Factor IIIA," *Nuc. Acids. Res.* 17(23):9861-9870 (1989).

Hayes et al., "Locations of Contacts Between Individual Zinc Fingers *Xenopus laevis* Transcription Factor IIIA and the Internal Control Region of a 5S RNA Gene," *Biochemistry* 31:11600-11605 (1992).

Heinzel et al., "A Complex containing N-CoR, MSin3 and Histone Deacetylese Medates Transcriptional Repression," *Nature* 387:43-48 (1997).

Hirst et al., "Discrimination of DNA Response Elements for Thyroid Hormone and Estrogen is Dependent on Dimerization of Receptor DNA Binding Domains," *PNAS* 89 :5527-5531 (1992).

Hoffman et al., "Structures of DNA-Binding Mutant Zinc Finger Domains: Implications for DNA Binding," *Protein Science* 2:951-965 (1993).

Isalan et al., "Synergy Between Adjacent Zinc Fingers in Sequence-Specific DNA Recognition," *PNAS* 94(11):5617-5621 (1997).

Isalan et al., "Comprehensive DNA Recognition Through Concerted Interactions from Adjacent Zinc Fingers," *Biochemistry* 37:12026-12033 (1998).

Jacobs, G.H., "Determination of the Base Recognition Positions of Zinc Fingers From Sequence Analysis," *EMBO J.* 11(12):4507-4517 (1992).

Jamieson et al. "A Zinc Finger Directory for High-Affinity DNA Recognition," *PNAS* 93:12834-12839 (1996).

Jamieson et al., "In Vitro Selection of Zinc Fingers with Altered DNA-Binding Specificity" *Biochemistry* 33:5689-5695 (1994).

Julian et al., "Replacement of His23 by Cys in a Zinc Finger of HIV-1NCp7 Led to a Change in 1H NMR-Derived 3D Structure and to a Loss of Biological Activity," *FEBS Letters* 331(1,2):43-48 (1993).

Kamiuchi et al., "New Multi Zinc Finger Protein: Biosynthetic Design and Characteristics of DNA Recognition," *Nucleic Acids Symposium Series* 37:153-154 (1997).

Kang et al., "Zinc Finger Proteins as Designer Transcription Factors," *J. Biol. Chem.* 275(12):8742-8748 (2000).

Kim et al., "Serine at Position 2 in the DNA Recogntion Helix of a Cys2-His2 Zinc Finger Peptide is Not, in General, Responsible for Base Recognition," *J. Mol. Biol.* 252:1-5 (1995).

Kim et al., "Site-Specific Cleavage of DNA-RNA Hybrids by Zinc Finger/*FokI* Cleavage Domain Fusions," *Gene* 203:43-49 (1997).

Kim et al., "A 2.2 Å Resolution Crystal Structure of a Designed Zinc Finger Protein Bound to DNA," *Nat. Struct. Biol.* 3(11):940-945 (1996).

Kim et al., "Design of TATA Box-Binding Protein/Zinc Finger Fusions for Targeted Regulation of Gene Expression," *PNAS* 94:3616-3620 (1997).

Kim et al., "Hybrid Restriction Enzymes: Zinc Finger Fusions *Fok* I Cleavage Domain," *PNAS* 93:1156-1160 (1996).

Kim et al. "Transcriptional repression by zinc finger peptides. Exploring the potential for applications in gene therapy" *J. Biol. Chem.* 272:29795-29800 (1997).

Kim et al. "Getting a handhold on DNA: design of poly-zinc finger proteins with femtomolar dissociation constants" *Proc. Natl. Acad. Sci. USA* 95:2812-2817 (1998).

Kinzler et al., "The GLI Gene is Member of the Kruppel Family of Zinc Finger Proteins," *Nature* 332:371-374 (1988).

Klug, A., "Gene Regulatory Proteins and Their Interaction with DNA," *Ann. NY Acad. Sci.* 758:143-160 (1995).

Klug et al., "Protein Motifs 5: Zinc Fingers," *FASEB J.* 9:597-604 (1995).

Klug, "Zinc Finger Peptides for the Regulation of Gene Expression," *J. Mol. Biol.* 293:215-218 (1999).

Kothekar, "Computer Simulation of Zinc Finger Motif from Cellular Nucleic Acid Binding Proteins and Their Interaction with Consensus DNA Sequences," *FEBS Letters* 274(1,2):217-222 (1990).

Kriwacki et al. "Sequence-specific recognition of DNA by zinc finger peptides derived from the transcription factor Sp-1,"*Proc. Natl. Acad. Sci. USA* 89:9759-9763 (1992).

Kulda et al., "The Regulatory Gene areA Mediating Nitrogen Metabolite R in *Aspergillus nidulans* Mutations Affecting Specificity of Gene Activation Alter a Loop Residue of Putative Zinc Finger," *EMBO J.* 9(5):1355-1364 (1990).

Laird-Offringa et al., "RNA-Binding Proteins Tamed," *Nat. Structural Biol.* 5(8):665-668 (1998).

Liu et al., "Design of Polydactyl Zinc-Finger Proteins for Unique Addressing Within Complex Genomes," *Proc. Natl. Acad. Sci. U.S.A.* 94:5525-5530 (1997).

Mandel-Gutfreund et al., "Quantitative Parameters for Amino Acid-Base Interaction: Implication for Predication of Protein-DNA Binding Sites," *Nuc. Acids Res.* 26(10):2306-2312 (1998).

Margolin et al., "Kruppel-Associated Boxes are Potent Transcriptional Repression Domains," *PNAS* 91:4509-4513 (1994).

Mizushima et al., "pEF-BOS, a Powerful Mammilian Expression Vector," *Nuc. Acids. Res.* 18(17):5322 (1990).

Nakagama et al., "Sequence and Structural Requirements for High-Affinity DNA Binding by the WT1 Gene Product," *Molecular and Cellular Biology* 15(3):1489-1498 (1995).

Nardelli et al., "Zinc Finger-DNA Recognition: Analysis of Base Specificity by Site-Directed Mutagenesis," *Nucleic Acids Research* 20(16):4137-4144 (1992).

Nardelli et al., "Base Sequence Discrimination by Zinc-Finger DNA-Binding Domains," *Nature* 349:175-178 (1991).

Nekludova et al., "Distinctive DNA Conformation With Enlarged Major Groove is Found in Zn-Finger-DNA and Other Protein-DNA Complexes," *PNAS* 91:6948-6952 (1994).

Orkin et al., "Report and Recommendations of the Panel to Assess the NIH Investment in Research on Gene Therapy," (Dec. 7, 1995).

Pabo et al., "Systematic Analysis of Possible Hydrogen Bonds between Amino Acid Side Chains and B-form DNA," *J. Biomolecular Struct. Dynamic* 1:1039-1049 (1983).

Pabo et al., "Protein-DNA Recognition," *Ann. Rev. Biochem.* 53:293-321 (1984).

Pabo, C. O., "Transcription Factors: Structural Families and Principles of DNA Recognition," *Ann. Rev. Biochem.* 61:1053-1095 (1992).

Pavletich et al., "Crystal Structure of a Five-Finger GLI-DNA Complex: New Perspectives on Zinc Fingers," *Science*, 261:1701-1707 (1993).

Pavletich et al., "Zinc Finger-DNA Recognition: Crystal Structure of a Zif268-DNA Complex at 2.1 A," *Science* 252:809-817 (1991).

Pengue et al., "Repression of Transcriptional Activity at a Distance by the Evolutionarily Conserved KRAB Domain Present in a Subfamily of Zinc Finger Proteins," *Nuc. Acids Res.* 22(15):2908-2914 (1994).

Pengue et al., "Transcriptional Silencing of Human Immunodeficiency Virus Type I Long Terminal Repeat-Driven Gene Expression by the Kruppel-Associated Box Repressor Domain Targeted to the Transactivating Response Element," *J. Virology* 69(10):6577-6580 (1995).

Pengue et al., "Kruppel-Associated Box-Mediated Repression of RNA Polymerase II Promoters is Influenced by the Arrangement of Basal Promoter Elements," *PNAS* 93:1015-1020 (1996).

Pomerantz et al., "Analysis of Homeodomain Function by Structure-Based Design of a Transcription Factor," *PNAS* 92:9752-9756 (1995).

Pomerantz et al., "Structure-Based Design of a Dimeric Zinc. Finger Protein," *Biochemistry* 37(4):965-970 (1998).

Pomerantz et al., "Structure-Based Design of Transcription Factors," *Science* 267:93-96 (1995).

Qian et al., "Two-Dimensional NMR Studies of the Zinc Finger Motif:. Solution Structures and Dynamics of Mutant ZFY Domains Containing Aromatic Substitutions in the Hydrophobic Core," *Biochemistry* 31:7463-7476 (1992).

Quigley et al., "Complete Androgen Insensitivity Due to Deletion of Exon C of the Androgen Receptor Gene Highlights the Functional Importance of the Second Zinc Finger of the Androgen Receptor *in Vivo,*" *Molecular Endocrinology* 6(7):1103-1112 (1992).

Rauscher et al., "Binding of the Wilms' Tumor Locus Zinc Finger Protein to the EGR-I Consensus Sequence," *Science* 250:1259-1262 (1990).

Ray et al., "Repressor to Activator Switch by Mutations in the First Zn Finger of the Glucocorticoid Receptor: Is Direct DNA Binding Necessary?," *PNAS* 88:7086-7090 (1991).

Rebar et al., "Phage Display Methods for Selecting Zinc Finger Proteins with Novel DNA-Binding Specificities," *Methods in Enzymology* 267:129-149 (1996).

Rebar et al., "Zinc Finger Phage: Affinity Selection of Fingers With New DNA-Binding Specifities," *Science* 263:671-673 (1994).

Reith et al., "Cloning of the Major Histocompatibility Complex Class II Promoter Binding Protein Affected in a Herediatry Defect in Class II Gene Regulation," *PNAS* 86:4200-4204 (1989).

Rhodes et al., "Zinc Fingers: They Play a Key Part in Regulating the Activity of Genes in Many Species, From Yeast to Humans. Fewer Than 10 Years Ago No One Knew They Existed." *Scientific American* 268:56-65 (1993).

Rice et al., "Inhibitors of HIV Nucleocapsid Protein Zinc Fingers as Candidates for the Treatment of AIDS," *Science*. 270:1194-1197 (1995).

Rivera et al., "A Humanized System for Pharmacologic Control of Gene Expression," *Nature Medicine* 2(9):1028-1032 (1996).

Rollins et al., "Role of TFIIIA Zinc Fingers *In vivo*: Analysis of Single-Finger Function in Developing *Xenopus* Embryos," *Molecular Cellular Biology* 13(8):4776-4783 (1993).

Saleh et al., "A Novel Zinc Finger Gene on Human Chromosome 1 qter That is Alternatively Spliced in Human Tissues and Cell Lines," *American Journal of Human Genetics* 52:192-203 (1993).

Shi et al., "Specific DNA-RNA Hybrid Binding by Zinc Finger Proteins," *Science* 268:282-284 (1995).

Shi et al., "DNA Unwinding Induced by Zinc Finger Protein Binding," *Biochemistry* 35:3845-3848 (1996).

Shi et al., "A Direct Comparison of the Properties of Natural and Designed Finger Proteins," *Chem. & Biol.* 2(2):83-89 (1995).

Singh et al., "Molecular Cloning of an Enhancer Binding Protein: Isolation by Screening of an Expression Library with a Recognition Site DNA," *Cell* 52 :415-423 (1988).

Skerka et al., "Coordinate Expression and Distinct DNA-Binding Characteristics of the Four EGR-Zinc Finger Proteins in Jurkat T Lymphocytes," *Immunobiology* 198:179-191 (1997).

Smith et al., "A detailed study of the substrate specificity . . . ," *Nucleic Acids Research* 27(2):674-681 (1999).

South et al., "The Nucleocapsid Protein Isolated from HIV-1 Particles Binds Zinc and Forms Retroviral-Type Zinc Fingers," *Biochemistry* 29:7786-7789 (1990).

Suzuki et al., "Stereochemical Basis of DNA Recognition by Zn Fingers," *Nuc. Acids Res.* 22(16):3397-3405 (1994).

Suzuki et al. "DNA Recognition Code of Transcription Factors in the Helix-turn-Helix, Probe Helix, Hormone Receptor, and Zinc Finger Families," *PNAS* 91:12357-12361 (1994).

Swirnoff et al., "DNA-Binding Specificy of NGFI-A and Related Zinc Finger Transcription Factors," *Mol. Cell. Biol.* 15 (4):2275-2287 (1995).

Taylor et al., "Designing Zinc-Finger ADRI Mutants with Altered Specificity of DNA Binding to T in UASI Sequences," *Biochemistry* 34:3222-3230 (1995).

Thiesen et al., "Determination of DNA Binding Specificities of Mutated Zinc Finger Domains," *FEBS Letters* 283(1):23-26 (1991).

Thiesen et al., "Amino Acid Substitutions in the SP1 Zinc Finger Domain Alter the DNA Binding Affinity to Cognate SP1 Target Site," *Biochem. Biophys. Res. Communications* 175(1):333-338 (1991).

Thukral et al., "Localization of a Minimal Binding Domain and Activation Regions in Yeast Regulatory Protein ADRI1," *Molecular Cellular Biology* 9(6):2360-2369 (1989).

Thukral et al., "Two Monomers of Yeast Transcription Factor ADR1 Bind a Paldromic Sequence Symmetrically to Activate *ADH2* Expression," *Molecular Celluar Biol.* 11(3):1566-1577 (1991).

Thurkral et al., "Alanine Scanning Site-Directed Mutagenesis of the Zinc Fingers of Transcription Factor ADR1: Residues that Contact DNA and that Transactivate," *PNAS* 88:9188-9192 (1991), + correction page.

Thukral et al., "Mutations in the Zinc Fingers of ADR1 That Change the Specificity of DNA Binding and Transactivation," *Mol. Cell Biol.* 12(6):2784-2792 (1992).

Vortkamp et al., "Identification of Optimized Target Sequences for the GL13 Zinc Finger Protein," *DNA Cell Biol.* 14(7):629-634 (1995).

Wang et al., "Dimerization of Zinc Fingers Mediated by Peptides Evolved *In Vitro* From Random Sequences," *Proc. Natl. Acad. Sci. U.S.A.* 96:9568-9573 (1999).

Webster et al., "Conversion of the E1A Cys4 Zinc Finger to a Nonfunctional His2, Cys2 Zinc Finger by a Single Point Mutation," *PNAS* 88 :9989-9993 (1991).

Whyatt et al., "The Two Zinc Finger-Like Domains of GATA-1 Have Different DNA Binding Specificities," *EMBO J.* 12(13):4993-5005 (1993).

Wilson et al., "*In Vivo* Mutational Analysis of the NGFI-A Zinc Fingers," *J. Biol. Chem.* 267(6):3718-3724 (1992).

Witzgall et al., "The Kruppel-Associated Box-A (KRAB-A) Domain of Zinc Finger Proteins Mediates Transcriptional Repression" *PNAS* 91:4514-4518 (1994).

Wolfe et al., "Analysis of Zinc Fingers Optimized Via Phage Display: Evaluating the Utility of a Recognition Code," *J. Mol. Biol.* 285:1917-1934 (1999).

Wright et al., "Expression of a Zinc Finger Gene in HTLV-1 and HTLV-II Transformed Cells," *Science* 248:588-591 (1990).

Wu et al., "Building Zinc Fingers by Selection: Toward a Therapeutic Application," *PNAS* 92:344-348 (1995).

Yang et al., "Surface Plasmon Resonance Based Kinetic Studies of Zinc Finger-DNA Interaction," *J. Immunol. Methods* 183:175-182 (1995).

Yu et al., "A Hairpin Ribozyme Inhibits Expression of Diverse Strains of Human Immunodeficiency Virus Type 1," *PNAS* 90:6343-6344 (1993).

Search of Swissprot. Data Base Performed CA Aug. 2000.

\* cited by examiner

Fig. 2A    Zinc Finger Peptides
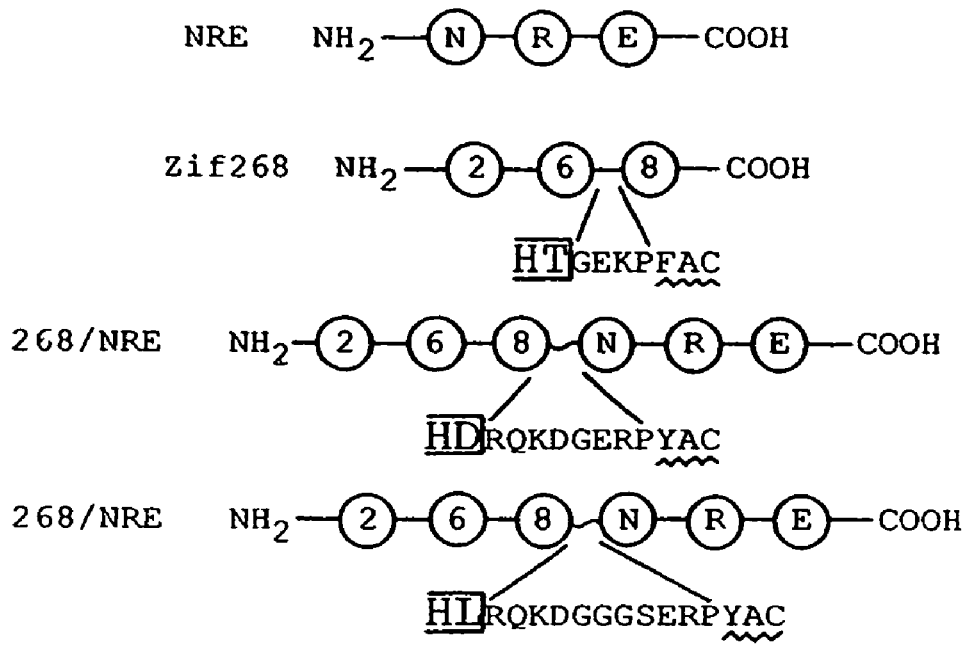
Fig. 2B    Promoters of Reporter Genes
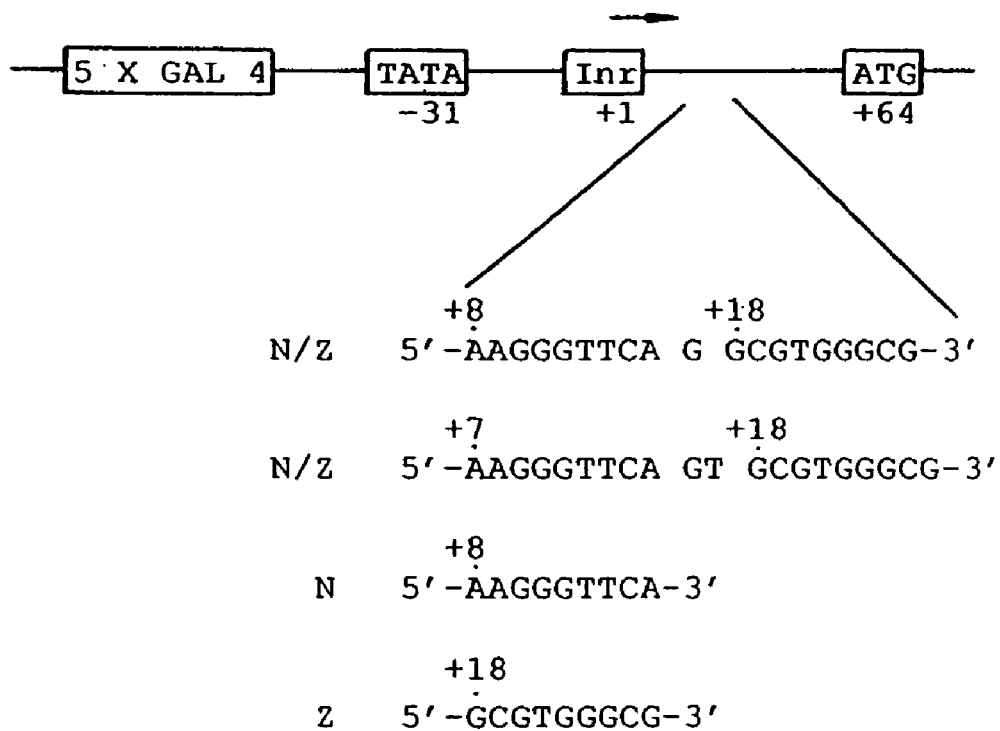

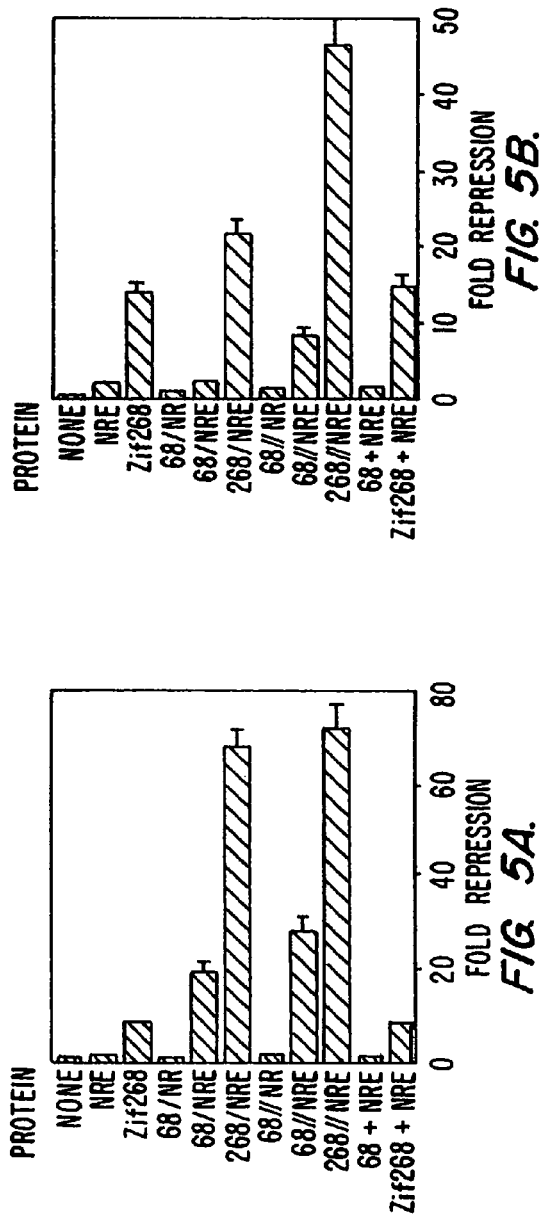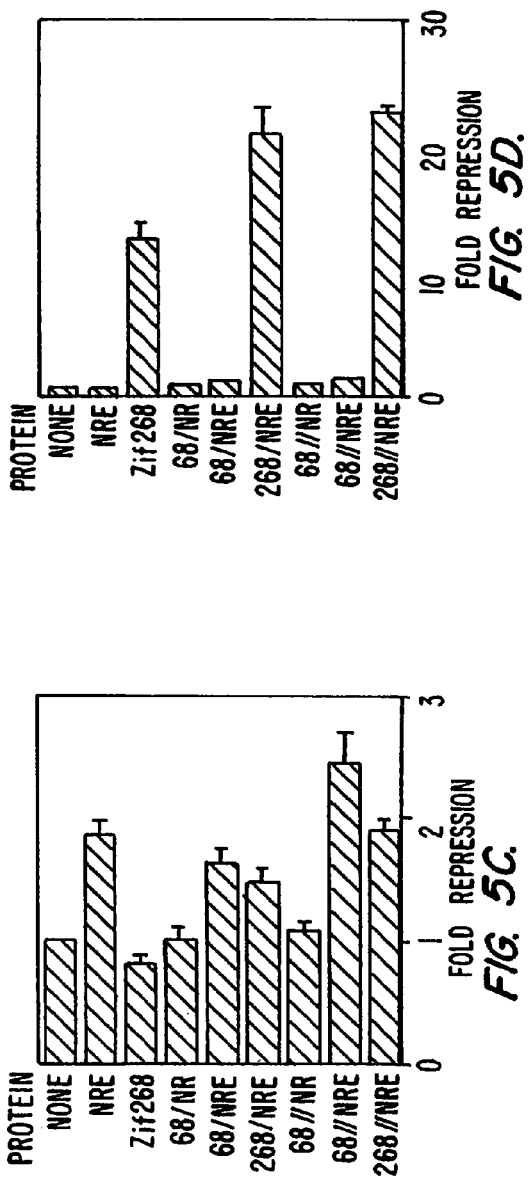

NUCLEIC ACID ENCODING POLY-ZINC FINGER PROTEINS WITH IMPROVED LINKERS

CROSS-REFERENCES TO RELATED APPLICATIONS

This application is a continuation of U.S. patent application Ser. No. 10/146,221, filed May 13, 2002, now U.S. Pat. No. 6,903,185, which is a continuation of U.S. patent application Ser. No. 09/260,629, filed Mar. 1, 1999, now U.S. Pat. No. 6,479,626, which claims the benefit under 35 USC 119(e)(1) of U.S. Provisional Patent Application No. 60/076,454, filed Mar. 2, 1998, all of which are herein incorporated by reference in their entirety.

STATEMENT AS TO INVENTIONS MADE UNDER FEDERALLY SPONSORED RESEARCH AND DEVELOPMENT

Work described herein was supported by grants PO1-CA42063, CDR-8803014 and P30-CA14051 from the National Institutes of Health, National Science Foundation and National Cancer Institute, respectively. The U.S. Government has certain rights in the invention. Work described herein was also supported by the Howard Hughes Medical Institute.

BACKGROUND OF THE INVENTION

Zinc fingers belonging to the $Cys_2$-$His_2$ family constitute one of the most common DNA-binding motifs found in eukaryotes, and these zinc fingers have provided a very attractive framework for the design and selection of DNA-binding proteins with novel sequence specificities. Numerous studies have used phage display methods or design ideas to explore and systematically alter the specificity of zinc finger-DNA interactions (Desjarlais & Berg, *Proteins Struct. Funct. Genet.* 12:101–104 (1992); Desjarlais & Berg, *Proc. Natl. Acad. Sci. USA* 90:2256–2260 (1993); Rebar & Pabo, *Science* 263:671–673 (1994); Jamieson et al., *Biochemistry* 33:5689–5695 (1994); Choo & Klug, *Proc. Natl. Acad Sci. USA* 91:11163–11167 (1994); Wu et al., *Proc. Natl. Acad. Sci. USA* 92:344–348 (1995); and Greisman & Pabo, *Science* 275:657–661 (1997)).

Structure based computer design has been used to link $Cys_2$-$His_2$ zinc fingers with other DNA-binding domains, including other zinc finger proteins, to generate hybrid proteins that recognize extended sites (Pomerantz et al., *Science* 267:93–96 (1995); Kim et al, *Proc. Natl. Acad. Sci. USA* 94:3616–3620 (1997)). For example, zinc finger proteins have been linked to a GAL4 dimerization domain to develop novel homo- and hetero-dimers (Pomerantz et al., *Biochemistry* 4:965–970 (1997)), and to a nuclease domain to generate novel restriction enzymes (Kim et al., *Proc. Nati. Acad. Sci. USA* 93:1156–1160 (1996)). Zinc finger/homeodomain fusion is being tested for potential applications in gene therapy (Rivera et al., *Nature Med.* 2:1028–1032 (1996)).

There also have been several attempts to increase affinity and specificity of zinc finger proteins by adding additional fingers to a three-finger protein (Rebar, (Ph.D. Thesis), *Selection Studies of Zinc Finger-NA Recognition*, Massachusetts Institute of Technology (1997); Shi, Y. (Ph.D. Thesis) *Molecular Mechanisms of Zinc Finger Protein-Nucleic Acid Interactions*, Johns Hopkins University (1995)) or by tandemly linking two three-finger proteins (Liu et al., *Proc. Natl. Acad. Sci. USA* 94:5525–5530 (1997)). However, these previous design strategies for poly-finger proteins, which all used canonical "TGEKP" linkers (linkers having the amino acid sequence threonine-glycine-glutarnate-lysine-proline) to connect the additional fingers, resulted in relatively modest increases in affinity. There is thus a need to develop linkers that provide enhanced affinity and specificity to chimeric zinc finger proteins.

SUMMARY OF THE INVENTION

The present invention therefore provides a method of using structure based design to select flexible linkers and make chimeric zinc finger proteins with enhanced affinity and specificity. The present invention also provides a method of making chimeric zinc finger proteins that have flexible linkers of 5 amino acids or more in length to make chimeric zinc finger proteins with enhanced affinity and specificity. Zinc finger proteins made using these methods have binding affinities in the femtomolar range and provide, e.g., high levels (more than about 70 fold) of transcriptional repression at a single target site. Such zinc finger proteins can be used for regulation of gene expression, e.g., as therapeutics, diagnostics, and for research applications such as functional genomics.

In one aspect, the present invention provides a method of making a chimeric zinc finger protein that binds to adjacent target sites, the method comprising the steps of: (i) selecting a first and a second DNA-binding domain polypeptide of the chimeric zinc finger protein, wherein at least one of the domains comprises a zinc finger polypeptide, and wherein the first domain binds to a first target site and the second domain binds to a second target site, which target sites are adjacent; (ii) using structure-based design to determine the physical separation between the first and second domains when they are individually bound to the first and second target sites; (iii) selecting a flexible linker that is at least 1–2 Å longer than the physical separation between the first and second domains; and (iv) fusing the first and second domains with the flexible linker, thereby making a chimeric zinc finger protein that binds to adjacent target sites.

In another aspect, the present invention provides a method of making a chimeric zinc finger protein that binds to adjacent target sites, the method comprising the steps of: (i) selecting a first and a second DNA-binding domain polypeptide of the chimeric zinc finger protein, wherein at least one of the domains comprises a zinc finger polypeptide, and wherein the first domain binds to a first target site and the second domain binds to a second target site, which target sites are adjacent; (ii) selecting a flexible linker that is five or more amino acids in length; and (iv) fusing the first and second domains with the flexible linker, thereby making a chimeric zinc finger protein that binds to adjacent target sites.

In another aspect, the present invention provides a chimeric zinc finger protein that binds to adjacent target sites, the chimeric zinc finger protein comprising: (i) a first and a second DNA-binding domain polypeptide of the chimeric zinc finger protein, wherein at least one of the domains comprises a zinc finger polypeptide, and wherein the first domain binds to a first target site and the second domain binds to a second target site, which target sites are adjacent; and (ii) a flexible linker that is at least 1–2 Å longer than the physical separation between the first and second domains when they are individually bound to the first and second target sites, as determined by structure-based modeling; wherein the first and second domains are fused with the flexible linker.

In another aspect, the present invention provides a chimeric zinc finger protein that binds to adjacent target sites, the chimeric zinc finger protein comprising: (i) a first and a second DNA-binding domain polypeptide of the chimeric zinc finger protein, wherein at least one of the domains comprises a zinc finger polypeptide, and wherein the first domain binds to a first target site and the second domain binds to a second target site, which target sites are adjacent; and (ii) a flexible linker that is five or more amino acids in length; wherein the first and second domains are fused with the flexible linker.

In one embodiment, the present invention provides nucleic acids encoding the chimeric zinc finger proteins.

In one embodiment, the first and the second domains are zinc finger polypeptides. In another embodiment, the zinc finger polypeptide is selected from the group consisting of Zif268 and NRE. In another embodiment, the zinc finger polypeptides are heterologous. In one embodiment, the first domain is a zinc finger polypeptide and the second domain comprises a heterologous DNA-binding domain polypeptide. In another embodiment, the chimeric zinc finger protein further comprises a regulatory domain polypeptide.

In one embodiment, the chimeric zinc finger protein has femtomolar affinity for the adjacent target sites. In another embodiment, the chimeric zinc finger protein has about 2–4 femtomolar affinity for the adjacent target sites.

In one embodiment, the flexible linker is 5, 8, or 11 amino acids in length. In another embodiment, the flexible linker has the sequence RQKDGERP or RQKDGGGSERP.

In one embodiment, the target sites are separated by one or two nucleotides.

In one embodiment, the adjacent target sites are separated by zero nucleotides and the flexible linker is five or six amino acids in length. In another embodiment, the adjacent target sites are separated by one nucleotide and the flexible linker is seven, eight, or nine amino acids in length. In another embodiment, the adjacent target sites are separated by two nucleotides and the flexible linker is ten, eleven, or twelve amino acids in length. In another embodiment, the adjacent target sites are separated by three nucleotides and the flexible linker is twelve or more amino acids in length.

BRIEF DESCRIPTION OF THE DRAWINGS

FIG. 2 depicts schematic representations of zinc finger peptides and of reporter constructs used in transfection studies described herein. FIG. 2A shows zinc finger peptides. Each finger is represented with a circle. The amino acid sequence of a linker in the Zif268 peptide (which has a canonical "TGEKP" linker; SEQ ID NO:13) is shown (residues 2 to 6 inclusive of SEQ ID NO:16), and longer linkers used to connect the three-finger peptides are indicated below (residues 2 to 10 inclusive of SEQ ID NO:17 and residues 2 to 13 inclusive of SEQ ID NO:18). In each case, the box on the left denotes the helical region and includes the second of the conserved His residues of the finger: the zigzag line denotes the first β-sheet of the next finger, which includes the first of the conserved Cys residues. FIG. 2B illustrates promoters of luciferase reporter genes. The nucleotide positions of the TATA box, the start codon, and zinc finger binding sites (N/Z=SEQ ID NO:10; N//Z=SEQ ID NO:11; N=SEQ ID NO:9; Z=SEQ ID NO:8) are numbered with respect to the transcription start site (+1).

FIG. 4 depicts competition binding studies.

FIG. 5 depicts graphs (FIGS. 5A, 5B, 5C, and 5D) illustrating transcriptional repression in vivo by zinc finger peptides. Human 293 cells were transfected as described (Cepek et al., Genes Dev. 10:2079–2088 (1996)) using the calcium phosphate precipitation method. Luciferase and β-galactosidase activities were measured 48 hours later. The luciferase activities were divided by corresponding β-galactosidase activities to yield the relative luciferase activities. Repression levels (fold repression) were obtained by dividing 1) the relative luciferase activities from the cells transfected with the empty expression plasmid by 2) those from the cells transfected with zinc finger expression plasmids. Different scales are used in graphs for the different reporters. The 68/NR, 68/NRE, 68//NR, and 68//NRE peptides are variants of six-finger fusion proteins that are missing one or two of the terminal fingers. Thus the 68/NR peptide contains fingers 2 and 3 of the Zif268 peptide fused (via the shorter of the two linkers) to fingers 1 and 2 of the NRE peptide. The data represent an average of three independent experiments, and the standard error of the mean is shown.

DETAILED DESCRIPTION OF THE INVENTION

I. Introduction

Figure 1:
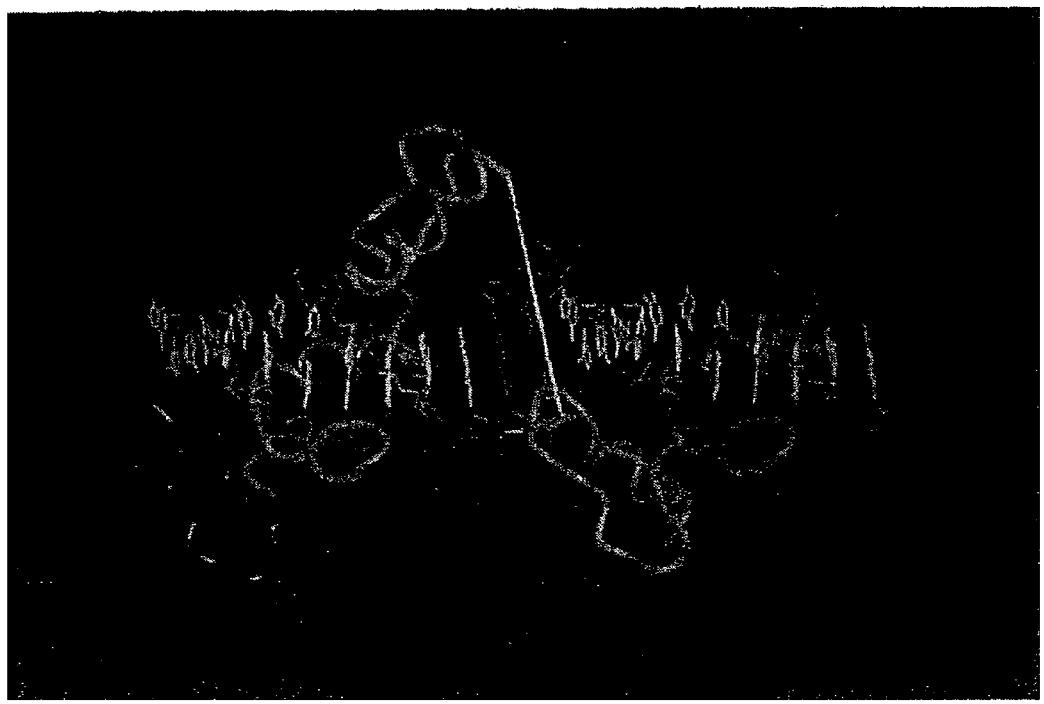
FIG. 1 depicts structure-based design of a six finger peptide, 268//NRE. The cocrystal structure of the Zif268-DNA complex and the template B-DNA (used at the junction) were aligned by superimposing phosphates (Pavletich & Pabo, Science 252:809–817 (1991); Elrod-Erickson et al., Structure 4:1171–1180 (1996)). In this model, two three-finger peptides bind to corresponding 9-bp sites (bases shown in white) separated by a 2 bp gap (bases shown in gray). Note that the orientation of one three-finger peptide almost exactly matches that of the other three finger peptide because one helical turn of this underwound DNA contains 11 bp.

The present invention provides a design strategy for linkers that fuse two DNA binding domains of a chimeric zinc finger protein. These linkers are flexible and longer than the canonical linkers previously used, allowing binding of the chimeric zinc finger protein to its target site without introducing any strain. The target site is typically a "composite" target site," composed of two adjacent target sites that are separated by zero to 5 or more nucleotides. Each of the adjacent target sites is recognized by one DNA-binding domain of the chimeric zinc finger protein. The linker design strategy involves structure-based design to determine a minimum length for a linker between two DNA-binding domains, and then adding additional amino acids to the linker to provide at least about 1–2 additional angstroms of flexibility to the linker. The present invention thus provides chimeric zinc finger proteins with femtomolar affinity for their target site, and which effectively repress gene expression, e.g., more than about 70 fold, when targeted to a single site.

Structural and biochemical analyses show that DNA often is slightly unwound when bound to zinc finger peptides (Pavletich & Pabo, Science 252:809–817 (1991); Shi & Berg, Biochemistry 35:3845–3848 (1996); Nekludova & Pabo, Proc. Natl. Acad. Sci. USA 91:6948–6952 (1994)). Modeling studies have shown that on ideal B DNA, the canonical linker is a bit too short to allow favorable docking of Zif268 (Elrod-Erickson et al., Structure 4:1171–1180 (1996)); the DNA must be slightly unwound to interact with zinc fingers in the mode seen in the Zif268 complex. Essentially, it appears that the helical periodicity of the zinc fingers does not quite match the helical periodicity of B-DNA. Since the strain of unwinding may become a more serious problem when there are more fingers (the helical periodicities of the peptide and DNA may get progressively further out of phase), longer, more flexible linkers were tested in the design of poly-finger proteins (see Kim & Pabo, Proc. Nat'l Acad Sci. U.S.A. 95:2812–2817 (1998), herein incorporated by reference in its entirety).

The present invention demonstrates that linkers of 5 amino acids or more can be used to make chimeric zinc finger proteins with enhanced affinity. For example, a linker of 8 amino acids was used for a chimeric zinc finger protein that recognized adjacent target sites separated by one base pair. A linker of 11 amino acids was used for a chimeric zinc finger protein that recognized adjacent target sites separated by two base pairs. The linkers of the invention can also be designed using structure-based modeling. In structure-based modeling, a model is made that shows the binding of each DNA binding domain polypeptide to its DNA target site. The model is then used to determine the physical separation of the domains as they are bound to adjacent target sites. The physical separation between the domains is used to determine the minimum length of the linker used to connect the C-terminal amino acid of the first domain with the N-terminal amino acid of the second domain, without steric hindrance to the linker or the DNA binding domains. This length is then increased by 1–2 Å, to create a slightly longer, flexible linker that avoids introducing strain to the chimeric zinc finger protein.

Often computer programs are used for structure-based modeling, although the models can also be made physically. Examples of computer programs used for structure-based modeling include Insight II (Biosym Technologies, San Diego) and Quanta 4.0 (Molecular Simulations (Burlington, Mass.). The programs often use information derived from x-ray crystallographic studies of DNA-binding proteins to provide the appropriate coordinates for proteins. This information can also be obtained from publicly available databases such as the Brookhaven Protein Data Bank. This information can also be used to extrapolate distances and coordinates for DNA binding proteins whose crystal structure is unknown. Models of B DNA are well known in the art. The relevant coordinates (e.g., distances and sizes) are used with computer modeling program of choice, using the manufacture's instructions and default parameters. Alternatively, customized parameters can be used. Structure-based modeling can be performed as described in, e.g., Kim & Pabo, Proc. Nat'l Acad. Sci. U.S.A. 95:2812–2817 (1998); Pavletich & Pabo, Science 252:809–817 (1991); Rebar, Ph.D. Thesis (Massachusetts Institute of Technology, Cambridge Mass.) (1997), Liu et al., Proc. Nat'l. Acad. Sci. U.S.A. 94:5525–5530 (1997); Pomerantz et al., Science 267:93–96 (1995); Pomerantz et al., Proc. Nat'l. Acad. Sci. U.S.A. 92:9752–9756 (1995); Li et al., Nature Biotechnology 16:190–195 (1998); Kim et al., Proc. Natl. Acad. Sci. USA 94:3616–3620 (1997); and Pomerantz et al., Biochemistry 4:965–970 (1997), herein incorporated by reference in their entirety). Two basic criteria suggest which alignments of DNA-binding domains have potential for combination in a chimeric protein which binds DNA: (1) lack of collision between domains, and (2) consistent positioning of the carboxyl- and amino-terminal regions of the domains, i.e., the domains are oriented such that the carboxyl-terminal region of one polypeptide can be joined to the amino-terminal region of the next polypeptide The linker used to link the two DNA-binding domains can comprise any amino acid sequence that does not substantially hinder interaction of the DNA-binding domains with their respective target sites. Preferred amino acid residues for linkers of the present invention include, but are not limited to glycine, alanine, leucine, serine, valine and threonine. Once the length of the amino acid sequence has been selected, the sequence of the linker can be selected, e.g., by phage display library technology (see, e.g., U.S. Pat. No. 5,260,203), or using naturally occurring or synthetic linker sequences as a scaffold (e.g., GTGQKP and GEKP, see Liu et al., Proc. Nat'l Acad. Sci. U.S.A. 94:5525–5530 (1997); see also Whitlow et al., Methods: A Companion to Methods in Enzymology 2:97–105 (1991)). Typically, the linkers of the invention are made by making recombinant nucleic acids encoding the linker and the DNA-binding domains, which are fused via the linker amino acid sequence. Optionally, the linkers can also be made using peptide synthesis, and then linked to the polypeptide DNA-binding domains.

The chimeric zinc finger proteins of the invention are composed of two or more DNA-binding domains, where at least one of the DNA binding domains is a zinc finger polypeptide. The second DNA binding domain can be a zinc finger binding domain, either the same domain or a heterologous domain. Suitable zinc finger proteins include any protein from the $Cys_2-His_2$ family, e.g., SP-1, SP-1C, ZIF268, NRE, Tramtrack, GLI, YY1, or TFIIIA (see, e.g., Jacobs, EMBO J. 11:4507 (1992); Desjarlais & Berg, PNAS 90:2256–2260 (1993); Christy et al., PNAS 85:7857–7861 (1988); Greisman & Pabo, Science 275:657–661 (1997); Fairall et al., Nature 366:483 (1993); Paveltich et al., Science 261:1701 (1993)).

The second DNA binding domain can also be a heterologous DNA binding domain, e.g., from a restriction enzyme; a nuclear hormone receptor; a homeodomain protein or a helix turn helix motif protein such as MAT 1, MAT 2, MAT a1, Antennapedia, Ultrabithorax, Engrailed, Paired, Fushi tarazu, HOX, Unc86, Oct1, Oct2, Pit, lambda repressor and tet repressor; Gal 4; TATA binding protein; helix loop helix motif proteins such as myc, myo D, Daughterless, Achaete-scute (T3), E12, and E47; leucine zipper type proteins such as GCN4, C/EBP, c-Fos/c-Jun and JunB; and beta sheet motif proteins such as met, arc, and mnt repressors. In another embodiment, the zinc finger protein is linked to at least one or more regulatory domains, described below. Preferred regulatory domains include transcription factor repressor or activator domains such as KRAB and VP16, co-repressor and co-activator domains, DNA methyl transferases, histone acetyltransferases, histone deacetylases, and endonucleases such as Fok1. The amino acid sequences of the DNA-binding domains may be naturally-occurring or non-naturally-occurring (or modified).

This invention pertains to proteins with novel nucleic acid binding specificities, particularly proteins which bind DNA and are comprised of two or more separate DNA-binding domains which do not occur together in the same arrangement in nature (i.e., are comprised of two or more separate DNA-binding domains which a) do not occur together in nature; b) do not occur together in nature in the order in which they are present in a chimeric protein of the present invention; or c) do not occur together in nature with the spacing that is present in ca chimeric protein of the present invention). In addition, the proteins of the present invention display DNA-binding specificity that is clearly distinct from that of the component DNA-binding domains; that is, they prefer binding the entire composite nucleotide sequence to binding a portion thereof. Two criteria suggest which arrangements of domains are suitable for combination in a chimeric protein which binds DNA: (1) lack of collision between component domains, and (2) consistent positioning of the carboxyl- and amino-terminal regions of each domain. Because of their ability to bind DNA normally bound by two or more separate DNA-binding domains which do not occur together in the same arrangement in nature, the proteins of the present invention are referred to as chimeric DNA-binding proteins.

The expression of chimeric zinc finger proteins can be also controlled by systems typified by the tet-regulated systems and the RU-486 system (see, e.g., Gossen & Bujard, *PNAS* 89:5547 (1992); Oligino et al., *Gene Ther.* 5:491–496 (1998); Wang et al, *Gene Ther.* 4:432–441 (1997); Neering et al., *Blood* 88:1147–1155 (1996); and Rendahl et al;, *Nat. Biotechnol.* 16:757–761 (1998)). These impart small molecule control on the expression of the chimeric zinc finger protein and thus impart small molecule control on the target gene(s) of interest. This beneficial feature could be used in cell culture models, in gene therapy, and in transgenic animals and plants.

The binding specificity of the chimeric DNA-binding proteins makes them particularly useful because they have DNA-binding properties distinct from those of known proteins. The chimeric proteins prefer to bind the adjacent target sites and, thus, can be used to modulate expression of genes having the adjacent target sites. These chimeric zinc finger proteins have an affinity for the adjacent target sites that is in the femtomolar range, e.g., 100 femtomoles, 10 femtomoles, or less, in some cases as low as 2–4 femtomoles, and in some cases 1 femtomolar or lower.

The zinc finger proteins made using the method of the invention have numerous applications, including therapeutic, diagnostic, and research applications such as in cell or animal models and functional genomics. For example, zinc finger proteins can be used to regulate gene expression, allowing for novel human and mammalian therapeutic applications, e.g., treatment of genetic diseases, cancer, fungal, protozoal, bacterial, and viral infection, ischemia, vascular disease, arthritis, immunological disorders, etc., as well as providing means for developing plants with altered phenotypes, including disease resistance, fruit ripening, sugar and oil composition, yield, and color. In addition, the zinc finger proteins of the present invention can be used for diagnostic assays and for functional genomics assays.

As described herein, zinc finger proteins can be designed to recognize any suitable target site for any of the uses described herein, e.g., eukaryotic and prokaryotic genes, cellular genes, viral genes, protozoal genes, fungal genes, and bacterial genes. In general, suitable genes to be regulated include cytokines, lymphokines, growth factors, mitogenic factors, chemotactic factors, onco-active factors, receptors, potassium channels, G-proteins, signal transduction molecules, and other disease-related genes.

A general theme in transcription factor function is that simple binding and sufficient proximity to the promoter are all that is generally needed. Exact positioning relative to the promoter, orientation, and within limits, distance do not matter greatly. This feature allows considerable flexibility in choosing sites for constructing zinc finger proteins. The target site recognized by the zinc finger protein therefore can be any suitable site in the target gene that will allow activation or repression of gene expression by a zinc finger protein, optionally linked to a regulatory domain.

Preferred target sites include regions adjacent to, downstream, or upstream of the transcription start site. In addition, target sites that are located in enhancer regions, repressor sites, RNA polymerase pause sites, and specific regulatory sites (e.g., SP-1 sites, hypoxia response elements, nuclear receptor recognition elements, p53 binding sites), sites in the cDNA encoding region or in an expressed sequence tag (EST) coding region. As described below, typically each finger recognizes 2–4 base pairs, with a two finger zinc finger protein binding to a 4 to 7 bp target site, a three finger zinc finger protein binding to a 6 to 10 base pair site, and a six finger zinc finger protein binding to two adjacent target sites, each target site having from 6–10 base pairs.

Chimeric zinc finger proteins of the invention can be tested for activity in vivo using a simple assay (*Current Protocols in Molecular Biology* (Ausubel et al., eds, 1994)). The in vivo assay uses a plasmid encoding the chimeric zinc finger protein, which is co-expressed with a reporter plasmid containing a test gene, e.g., the luciferase gene, the chloramphenicol acetyl transferase (CAT) gene or the human growth hormone (hGH) gene, with a target site for the chimeric zinc finger protein. The two plasmids are introduced together into host cells. A second group of cells serves as the control group and receives a plasmid encoding the transcription factor and a plasmid containing the reporter gene without the binding site for the transcription factor.

The production of reporter gene transcripts or the amount of activity of the relevant protein is measured; if mRNA synthesis from the reporter gene or the amount of activity of the relevant protein is greater than that of the control gene, the transcription factor is a positive regulator of transcription. If reporter gene mRNA synthesis or the amount of activity of the relevant protein is less than that of the control, the transcription factor is a negative regulator of transcription.

Optionally, the assay may include a transfection efficiency control plasmid. This plasmid expresses a gene product independent of the reporter gene, and the amount of this gene product indicates roughly how many cells are taking up the plasmids and how efficiently the DNA is being introduced into the cells. The chimeric zinc finger protein can also be tested for modulation of an endogenous gene in vivo, using methods known to those of skill in the art.

In one embodiment, the present invention provides a fusion in which the three-finger Zif268 peptide was linked to a designed three-finger peptide (designated "NRE") that specifically recognizes a nuclear hormone response element (Greisman & Pabo, *Science* 275:657 (1997)). Gel shift assays indicate that this six-finger peptide, 268//NRE, binds to a composite 18 bp DNA site with a dissociation constant in the femtomolar range. The slightly longer linkers used in this fusion protein provide a dramatic improvement in DNA-binding affinity, working much better than the canonical "TGEKP" linkers that have been used in previous studies. Tissue culture transfection experiments also show that the 268//NRE peptide is an extremely effective repressor, giving 72-fold repression when targeted to a binding site close to the transcription start site. Using this strategy and linking peptides selected via phage display allows the design of novel DNA-binding proteins with extraordinary affinity and specificity for use in biological applications and gene therapy.

The new six-finger peptides bind far more tightly than previously reported poly-finger proteins which used a conventional "TGEKP" linker to connect two three-finger modules or to add additional fingers to a three-finger protein. Poly-finger proteins with canonical linkers had been tested by Rebar (Rebar, (Ph.D. Thesis), *Selection Studies of Zinc Finger-DNA Recognition, Massachusetts Institute of Technology* (1997)), by Shi (Shi, (Ph.D. Thesis), *Molecular Mechanisms of Zinc Finger Protein-Nucleic Acid Interactions*, Johns Hopkins University (1995)), and by Liu et al. (Liu et al., *Proc. Natl. Acad. Sci. USA* 94:5525–5530 (1997)). Each study compared binding of the new poly-finger protein (at the appropriate extended site) with binding of the original three-finger peptide. Using canonical linkers, a four-finger peptide bound 6.3 times more tightly than the corresponding three-finger peptide (Rebar (Ph.D. Thesis), *Selection Studies of Zinc Finger-DNA Recognition*, Massachusetts Institute of Technology (1997)), a five-finger construct showed no improvement in $K_d$ over the original three-finger peptide (Shi, (Ph.D. Thesis), *Molecular Mechanisms of Zinc Finger Protein-Nucleic Acid Interactions*, Johns Hopkins University (1995)), and six-finger peptides bound 58–74-fold more tightly than the corresponding three-finger peptides (Liu et al., *Proc. Natl. Acad. Sci. USA* 94:5525–5530 (1997)).

In contrast, the peptides described herein (see Example section) bind 6,000–90,000-fold more tightly than the original three-finger peptides. It seems likely that the longer linkers used in the 268/NRE and 268//NRE constructs must relieve some strain that accumulates when a larger set of fingers all are connected with canonical linkers. Presumably this involves a slight mismatch in the helical periodicity of the DNA and the preferred helical periodicity of the zinc fingers, causing them to fall slightly out of register, particularly when 4 or more fingers are connected via canonical linkers.

II. Definitions

As used herein, the following terms have the meanings ascribed to them unless specified otherwise.

The term "zinc finger protein" or "ZFP" or "zinc finger polypeptide" refers to a protein having DNA binding domains that are stabilized by zinc. The individual DNA binding domains are typically referred to as "fingers." A zinc finger protein has at least one finger, typically two fingers, three fingers, or six fingers. Each finger binds from two to four base pairs of DNA, typically three or four base pairs of DNA (the "subsite"). A zinc finger protein binds to a nucleic acid sequence called a target site or target segment. Each finger typically comprises an approximately 30 amino acid, zinc-chelating, DNA-binding subdomain. An exemplary motif characterizing one class of these proteins ($C_2H_2$ class) is -Cys—(X)$_{2-4}$—Cys—(X)$_{12}$—His—(X)$_{3-5}$-His (SEQ ID NO:21) (where X is any amino acid). Studies have demonstrated that a single zinc finger of this class consists of an alpha helix containing the two invariant histidine residues coordinated with zinc along with the two cysteine residues of a single beta turn (see, e.g., Berg & Shi, Science 271: 1081–1085 (1996)).

A "chimeric" zinc finger protein refers to a protein that has at least two DNA-binding domains, one of which is a zinc finger polypeptide, linked to the other domain via a flexible linker. The two domains can be the same or heterologous. Both domains can be zinc finger proteins, either the same zinc finger protein or heterologous zinc finger proteins. Alternatively, one domain can be a heterologous DNA-binding protein.

A "target site" is the nucleic acid sequence recognized by a zinc finger protein or a heterologous DNA-binding polypeptide. For a zinc finger protein, a single target site typically has about four to about ten base pairs. Typically, a two-fingered zinc finger protein recognizes a four to seven base pair target site, a three-fingered zinc finger protein recognizes a six to ten base pair target site, and a six fingered zinc finger protein recognizes two adjacent nine to ten base pair target sites.

A "subsite" is a subsequence of the target site, and corresponds to a portion of the target site recognized by a single finger, e.g., a 2–4 base subsite, typically a 3 base subsite. A target site comprises at least two, typically three, four, five, six or more subsites, one for each finger of the protein.

The term "adjacent target sites" refers to non-overlapping target sites that are separated by zero to about 5 base pairs.

The "physical separation" between two DNA-binding domains refers to the distance between two domains when they are bound to their respective target sites. This distance is used to determine a minimum length of a linker. A minimum length of a linker is the length that would allow the two domains to be connected without providing steric hindrance to the domains or the linker (a minimum linker). A linker that provides more than the minimum length is a "flexible linker."

"Structure based design" refers to methods of determining the length of minimum linkers and flexible linkers, using physical or computer models of DNA-binding proteins bound to their respective target sites.

"$K_d$" refers to the dissociation constant for the compound, i.e., the concentration of a compound (e.g., a zinc finger protein) that gives half maximal binding of the compound to its target (i.e., half of the compound molecules are bound to the target) under given conditions (i.e., when [target]<<$K_d$), as measured using a given assay system (see, e.g., U.S. Pat. No. 5,789,538). The assay system used to measure the $K_d$ should be chosen so that it gives the most accurate measure of the actual $K_d$ of the zinc finger protein. Any assay system can be used, as long is it gives an accurate measurement of the actual $K_d$ of the zinc finger protein. In one embodiment, the $K_d$ for the zinc finger proteins of the invention is measured using an electrophoretic mobility shift assay ("EMSA"), as described in herein. Unless an adjustment is made for zinc finger protein purity or activity, $K_d$ calculations may result in an underestimate of the true $K_d$ of a given zinc finger protein.

The phrase "adjacent to a transcription initiation site" refers to a target site that is within about 50 bases either upstream or downstream of a transcription initiation site. "Upstream" of a transcription initiation site refers to a target site that is more than about 50 bases 5' of the transcription initiation site (i.e., in the non-transcribed region of the gene).

The phrase "RNA polymerase pause site" is described in Updating et al., *Annu. Rev. Biochem.* 66:117–172 (1997).

The term "heterologous" is a relative term, which when used with reference to portions of a nucleic acid indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include an non-native (non-naturally occurring) nucleic acid that has integrated into the chromosome, or a non-native (non-naturally occurring) extrachromosomal nucleic acid. In contrast, a naturally translocated piece of chromosome would not be considered heterologous in the context of this patent application, as it comprises an endogenous nucleic acid sequence that is native to the mutated cell.

A "regulatory domain" refers to a protein or a protein domain that has an activity such as transcriptional modulation activity, DNA modifying activity, protein modifying activity and the like when tethered to a DNA binding domain, i.e., a zinc finger protein. Examples of regulatory domains include proteins or effector domains of proteins, e.g., transcription factors and co-factors (e.g., KRAB, MAD, ERD, SID, nuclear factor kappa B subunit p65, early growth response factor 1, and nuclear hormone receptors, VP16, VP64), endonucleases, integrases, recombinases, methyltransferases, histone acetyltransferases, histone deacetylases etc. Activators and repressors include co-activators and co-repressors (see, e.g., Utley et al., *Nature* 394:498–502 (1998)).

A "heterologous DNA-binding domain" refers to a DNA binding domain from a protein that is not a zinc finger protein, such as a restriction enzyme, a nuclear hormone receptor, a homeodomain protein such as engrailed or antenopedia, a bacterial helix turn helix motif protein such as lambda repressor and tet repressor, Gal 4. TATA binding protein, helix loop helix motif proteins such as myc and myo D, leucine zipper type proteins such as fos and jun, and beta sheet motif proteins such as met, arc, and mnt repressors.

"Humanized" refers to a non-human polypeptide sequence that has been modified to minimize immunoreactivity in humans, typically by altering the amino acid sequence to mimic existing human sequences, without substantially altering the function of the polypeptide sequence (see, e.g., Jones et al., *Nature* 321:522–525 (1986), and published UK patent application No. 8707252). Backbone sequences for the zinc finger proteins are preferably be selected from existing human $C_2H_2$ zinc finger proteins (e.g., SP-1). Functional domains are preferably selected from existing human genes, (e.g., the activation domain from the p65 subunit of NF-κB). Where possible, the recognition helix sequences will be selected from the thousands of existing zinc finger protein DNA recognition domains provided by sequencing the human genome. As much as possible, domains will be combined as units from the same existing proteins. All of these steps will minimize the introduction of new junctional epitopes in the chimeric zinc finger proteins and render the engineered zinc finger proteins less immunogenic.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide. The nucleotide sequences are displayed herein in the conventional 5'-3' orientation.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins. The polypeptide sequences are displayed herein in the conventional N-terminal to C-terminal orientation.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine, and methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon in an amino acid herein, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid and nucleic acid sequences, individual substitutions, deletions or additions that alter, add or delete a single amino acid or nucleotide or a small percentage of amino acids or nucleotides in the sequence create a "conservatively modified variant," where the alteration results in the substitution of an amino acid with a chemically similar amino acid. Conservative substitution tables providing functionally similar amino acids are well known in the art. Such conservatively modified variants are in addition to and do not exclude polymorphic variants and alleles of the invention.

The following groups each contain amino acids that are conservative substitutions for one another:
1) Alanine (A), Glycine (G);
2) Serine (S), Threonine (T);
3) Aspartic acid (D), Glutamic acid (E);
4) Asparagine (N), Glutamine (Q);
5) Cysteine (C), Methionine (M);
6) Arginine (R), Lysine (K), Histidine (H);
7) Isoleucine (I), Leucine (L); Valine (V); and
8) Phenylalanine (F), Tyrosine (Y), Tryptophan (W).
(see, e.g., Creighton, *Proteins* (1984) for a discussion of amino acid properties).

III. Design of Zinc Finger Proteins

The chimeric zinc finger proteins of the invention comprise at least one zinc finger polypeptide linked via a flexible linker to at least a second DNA binding domain, which optionally is a second zinc finger polypeptide. The chimeric zinc finger protein may contain more than two DNA-binding domains, as well as one or more regulator domains. The zinc finger polypeptides of the invention can be engineered to recognize a selected target site in the gene of choice. Typically, a backbone from any suitable $C_2H_2$ ZFP, such as SP-1, SP-1C, or ZIF268, is used as the scaffold for the engineered zinc finger polypeptides (see e.g., Jacobs, *EMBO J.* 11:4507 (1992); Desjarlais & Berg, *PNAS* 90:2256–2260 (1993)). A number of methods can then be used to design and select a zinc finger polypeptide with high affinity for its target. A zinc finger polypeptide can be designed or selected to bind to any suitable target site in the target gene, with high affinity. U.S. Pat. Nos. 6,453,242 and 6,785,613, herein incorporated by reference, comprehensively describe methods for design, construction, and expression of zinc finger polypeptides for selected target sites.

Any suitable method known in the art can be used to design and construct nucleic acids encoding zinc finger polypeptides, e.g., phage display, random mutagenesis, combinatorial libraries, computer/rational design, affinity selection, PCR, cloning from cDNA or genomic libraries, synthetic construction and the like. (see, e.g., U.S. Pat. No. 5,786,538; Wu et al., *PNAS* 92:344–348 (1995); Jamieson et al., *Biochemistry* 33:5689–5695 (1994); Rebar & Pabo, *Science* 263:671–673 (1994); Choo & Klug, *PNAS* 91:11163–11167 (1994); Choo & Klug, *PNAS* 91: 11168–11172 (1994); Desjarlais & Berg, *PNAS* 90:2256–2260 (1993); Desjarlais & Berg, *PNAS* 89:7345–7349 (1992); Pomerantz et al., *Science* 267:93–96 (1995); Pomerantz et al., *PNAS* 92:9752–9756 (1995); and Liu et al., *PNAS* 94:5525–5530 (1997); Griesman & Pabo, *Science* 275:657–661 (1997); Desjarlais & Berg, *PNAS* 91:11-99-11103 (1994)).

In a preferred embodiment, U.S. Pat. No. 6,453,242 provides methods that select a target gene, and identify a target site within the gene containing one to six (or more) D-able sites (see definition below). Using these methods, a zinc finger polypeptide can then be synthesized that binds to the preselected site. These methods of target site selection are premised, in part, on the recognition that the presence of one or more D-able sites in a target segment confers the potential for higher binding affinity in a zinc finger polypeptide selected or designed to bind to that site relative to zinc finger polypeptides that bind to target segments lacking D-able sites.

A D-able site or subsite is a region of a target site that allows and appropriately designed single zinc finger to bind to four bases rather than three of the target site. Such a zinc finger binds to a triplet of bases on one strand of a double-stranded target segment (target strand) and a fourth base on the other strand (see FIG. 2 of U.S. Pat. No. 6,453,242). Binding of a single zinc finger to a four base target segment imposes constraints both on the sequence of the target strand and on the amino acid sequence of the zinc finger. The target site within the target strand should include the "D-able" site motif 5' NNGK 3', in which N and K are conventional IUPAC-IUB ambiguity codes. A zinc finger for binding to such a site should include an arginine residue at position–1 and an aspartic acid, (or less preferably a glutamic acid) at position+2. The arginine residues at position–1 interacts with the G residue in the D-able site. The aspartic acid (or glutamic acid) residue at position+2 of the zinc finger interacts with the opposite strand base complementary to the K base in the D-able site. It is the interaction between aspartic acid (symbol D) and the opposite strand base (fourth base) that confers the name D-able site. As is apparent from the D-able site formula, there are two subtypes of D-able sites: 5' NNGG 3' and 5' NNGT 3'. For the former site, the aspartic acid or glutamic acid at position+2 of a zinc finger interacts with a C in the opposite strand to the D-able site. In the latter site, the aspartic acid or glutamic acid at position+2 of a zinc finger interacts with an A in the opposite strand to the D-able site. In general, NNGG is preferred over NNGT.

In the design of a zinc finger polypeptide with three fingers, a target site should be selected in which at least one finger of the protein, and optionally, two or all three fingers have the potential to bind a D-able site. Such can be achieved by selecting a target site from within a larger target gene having the formula 5'-NNx aNy bNzc-3', wherein each of the sets (x, a), (y, b) and (z, c) is either (N, N) or (G, K);

at least one of (x, a), (y, b) and (z, c) is (G, K) and

N and K are IUPAC-IUB ambiguity codes

In other words, at least one of the three sets (x, a), (y, b) and (z, c) is the set (G, K), meaning that the first position of the set is G and the second position is G or T. Those of the three sets (if any) which are not (G, K) are (N, N), meaning that the first position of the set can be occupied by any nucleotide and the second position of the set can be occupied by any nucleotide. As an example, the set (x, a) can be (G, K) and the sets (y, b) and (z, c) can both be (N, N).

In the formula 5'-NNx aNy bNzc-3', the triplets of NNx aNy and bNzc represent the triplets of bases on the target strand bound by the three fingers in a zinc finger polypeptide. If only one of x, y and z is a G, and this G is followed by a K, the target site includes a single D-able subsite. For example, if only x is G, and a is K, the site reads 5'-NNG KNy bNzc-3' with the D-able subsite highlighted. If both x and y but not z are G, and a and b are K, then the target site has two overlapping D-able subsites as follows: 5'-NNG KNz KNz c-3', with one such site being represented in bold and the other in italics. If all three of x, y and z are G and a, b, and c are K, then the target segment includes three D-able subsites, as follows 5'NNG KNG KNGK3', the D-able subsites being represented by bold, italics and underline.

These methods thus work by selecting a target gene, and systematically searching within the possible subsequences of the gene for target sites conforming to the formula 5'-NNx aNy bNzc-3', as described above. In some such methods, every possible subsequence of 10 contiguous bases on either strand of a potential target gene is evaluated to determine whether it conforms to the above formula, and, if so, how many D-able sites are present. Typically, such a comparison is performed by computer, and a list of target sites conforming to the formula are output. Optionally, such target sites can be output in different subsets according to how many D-able sites are present.

In a variation, the methods of the invention identify first and second target segments, each independently conforming to the above formula. The two target segments in such methods are constrained to be adjacent or proximate (i.e., within about 0–5 bases) of each other in the target gene. The strategy underlying selection of proximate target segments is to allow the design of a zinc finger polypeptide formed by linkage of two component zinc finger polypeptides specific for the first and second target segments respectively. These principles can be extended to select target sites to be bound by zinc finger polypeptides with any number of component fingers. For example, a suitable target site for a nine finger protein would have three component segments, each conforming to the above formula.

The target sites identified by the above methods can be subject to further evaluation by other criteria or can be used directly for design or selection (if needed) and production of a zinc finger polypeptide specific for such a site. A further criteria for evaluating potential target sites is their proximity to particular regions within a gene. If a zinc finger polypeptide is to be used to repress a cellular gene on its own (i.e., without linking the zinc finger polypeptide to a repressing moiety), then the optimal location appears to be at, or within 50 bp upstream or downstream of the site of transcription initiation, to interfere with the formation of the transcription complex (Kim & Pabo, *J. Biol. Chem.* 272:29795–296800 (1997)) or compete for an essential enhancer binding protein. If, however, a zinc finger polypeptide is fused to a functional domain such as the KRAB repressor domain or the VP16 activator domain, the location of the binding site is considerably more flexible and can be outside known regulatory regions. For example, a KRAB domain can repress transcription at a promoter up to at least 3 kbp from where KRAB is bound (Margolin et al., *PNAS* 91:4509–4513 (1994)). Thus, target sites can be selected that do not necessarily include or overlap segments of demonstrable biological significance with target genes, such as regulatory sequences. Other criteria for further evaluating target segments include the prior availability of zinc finger polypeptide s binding to such segments or related segments, and/or ease of designing new zinc finger polypeptides to bind a given target segment.

After a target segment has been selected, a zinc finger polypeptide that binds to the segment can be provided by a variety of approaches. The simplest of approaches is to provide a precharacterized zinc finger polypeptide from an existing collection that is already known to bind to the target site. However, in many instances, such zinc finger polypeptides do riot exist. An alternative approach can also be used to design new v zinc finger polypeptides, which uses the information in a database of existing zinc finger polypeptides and their respective binding affinities. A further approach is to design a zinc finger polypeptide based on substitution rules as discussed above. A still further alternative is to select a zinc finger polypeptide with specificity for a given target by an empirical process such as phage display. In some such methods, each component finger of a zinc finger polypeptide is designed or selected independently of other component fingers. For example, each finger can be obtained from a different preexisting zinc finger polypeptide or each finger can be subject to separate randomization and selection.

Once a zinc finger polypeptide has been selected, designed, or otherwise provided to a given target segment, the zinc finger polypeptide or the DNA encoding it are synthesized. Exemplary methods for synthesizing and expressing DNA encoding zinc finger proteins are described below. The zinc finger polypeptide or a polynucleotide encoding it can then be used for modulation of expression, or analysis of the target gene containing the target site to which the zinc finger polypeptide binds.

IV. Expression and Purification of Zinc Finger Proteins Made Using the Methods of the Invention Chimeric zinc finger proteins comprising a flexible linker and nucleic acids encoding such chimeric zinc finger proteins can be made using routine techniques in the field of recombinant genetics. Basic texts disclosing the general methods of use in this invention include Sambrook et al., *Molecular Cloning A Laboratory Manual* (2nd ed. 1989); Kriegler, *Gene Transfer and Expression: A Laboratory Manual* (1990); and *Current Protocols in Molecular Biology* (Ausubel et al., eds., 1994)). In addition, essentially any nucleic acid can be custom ordered from any of a variety of commercial sources. Similarly, peptides and antibodies can be custom ordered from any of a variety of commercial sources.

Two alternative methods are typically used to create the coding sequences required to express newly designed DNA-binding polypeptides and the flexible linker. One protocol is a PCR-based assembly procedure that utilizes six overlapping oligonucleotides.(to make one three finger zinc finger polypeptide). Three oligonucleotides correspond to "universal" sequences that encode portions of the DNA-binding domain between the recognition helices. These oligonucleotides remain constant for all zinc finger constructs. The other three "specific" oligonucleotides are designed to encode the recognition helices. These oligonucleotides contain substitutions primarily at positions −1, 2, 3 and 6 on the recognition helices making them specific for each of the different zinc fingers.

To make a three finger zinc finger polypeptide, the PCR synthesis is carried out in two steps. First, a double stranded DNA template is created by combining the six oligonucleotides (three universal, three specific) in a four cycle PCR reaction with a low temperature annealing step, thereby annealing the oligonucleotides to form a DNA "scaffold." The gaps in the scaffold are filled in by high-fidelity thermostable polymerase, the combination of Taq and Pfu polymerases also suffices. In the second phase of construction, the zinc finger template is amplified by external primers designed to incorporate restriction sites at either end for cloning into a shuttle vector or directly into an expression vector.

An alternative method of cloning the newly designed DNA-binding proteins relies on annealing complementary oligonucleotides encoding the specific regions of the desired chimeric zinc finger protein. This particular application requires that the oligonucleotides be phosphorylated prior to the final ligation step. This is usually performed before setting up the annealing reactions, but kinasing can also occur post-annealing. In brief, the "universal" oligonucleotides encoding the constant regions of the proteins (oligos 1, 2 and 3 of above) are annealed with their complementary oligonucleotides. Additionally, the "specific" oligonucleotides encoding the finger recognition helices are annealed with their respective complementary oligonucleotides. These complementary oligos are designed to fill in the region which was previously filled in by polymerase in the protocol described above. The complementary oligos to the common oligos 1 and finger 3 are engineered to leave overhanging sequences specific for the restriction sites used in cloning into the vector of choice. The second assembly protocol differs from the initial protocol in the following aspects: the "scaffold" encoding the newly designed ZFP is composed entirely of synthetic DNA thereby eliminating the polymerase fill-in step, additionally the fragment to be cloned into the vector does not require amplification. Lastly, the design of leaving sequence-specific overhangs eliminates the need for restriction enzyme digests of the inserting fragment.

The resulting fragment encoding the newly designed zinc finger polypeptide is ligated into an expression vector. The sequences encoding the flexible linker and the second DNA-binding domain (optionally a zinc finger polypeptide) are also ligated into the vector to create a chimeric zinc finger proteins. Typically, the flexible linker is encoded by a oligonucleotide that is ligated into the expression vector between the two DNA binding domains. The second DNA binding domain can be made as described above, or can be cloned or obtained from an alternative source using methods well known in the art, e.g., PCR and the like. Expression vectors that are commonly utilized include, but are not limited to, a modified pMAL-c2 bacterial expression vector (New England BioLabs, "NEB") or a eukaryotic expression vector, pcDNA (Promega).

The nucleic acid encoding the chimeric zinc finger protein of choice is typically cloned into intermediate vectors for transformation into prokaryotic or eukaryotic cells for replication and/or expression, e.g., for determination of $K_d$. Intermediate vectors are typically prokaryote vectors, e.g., plasmids, or shuttle vectors, or insect vectors, for storage or manipulation of the nucleic acid encoding zinc finger protein or production of protein. The nucleic acid encoding a zinc finger protein is also typically cloned into an expression vector, for administration to a plant cell, animal cell, preferably a mammalian cell or a human cell, fungal cell, bacterial cell, or protozoal cell.

To obtain expression of a cloned gene or nucleic acid, a chimeric zinc finger protein is typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). Bacterial expression systems for expressing the zinc finger protein are available in, e.g., *E. coli*, *Bacillus* sp., and *Salmonella* (Palva et al., *Gene* 22:229–235 (1983)). Kits for such expression systems are commercially available. Eukaryotic expression systems for mammalian cells, yeast, and insect cells are well known in the art and are also commercially available.

The promoter used to direct expression of a chimeric zinc finger protein nucleic acid depends on the particular application. For example, a strong constitutive promoter is typically used for expression and purification of zinc finger protein. In contrast, when a zinc finger protein is administered in vivo for gene regulation, either a constitutive or an inducible promoter is used, depending on the particular use of the zinc finger protein. The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard, *Proc. Natl. Acad Sci. U.S.A.* 89:5547 (1992); Oligino et al., *Gene Ther.* 5:491–496 (1998); Wang et al., *Gene Ther.* 4:432–441 (1997); Neering et al., *Blood* 88:1147–1155 (1996); and Rendahl et al., *Nat. Biotechnol.* 16:757–761 (1998)).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the zinc finger protein, and signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the zinc finger protein, e.g., expression in plants, animals, bacteria, fungus, protozoa, etc. Standard bacterial expression vectors include plasmids such as pBR322 based plasmids, pSKF, pET23D, and commercially available fusion expression systems such as GST and LacZ. A preferred fusion protein is the maltose binding protein, "MBP." Such fusion proteins are used for purification of the zinc finger protein. Epitope tags can also be added to recombinant proteins to provide convenient methods of isolation, for monitoring expression, and for monitoring cellular and subcellular localization, e.g., c-myc or FLAG.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with a zinc finger protein encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., *J. Biol. Chem.* 264:17619–17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Any suitable method of protein purification known to those of skill in the art can be used to purify the chimeric zinc finger proteins of the invention (see Ausubel, supra; Sambrook, supra). In addition, any suitable host can be used, e.g., bacterial cells, insect cells, yeast cells, mammalian cells, and the like.

In one embodiment, expression of the zinc finger protein fused to a maltose binding protein (MBP-zinc finger protein) in bacterial strain JM109 allows for straightforward purification through an amylose column (NEB). High expression levels of the chimeric zinc finger protein can be obtained by induction with IPTG since the MBP-zinc finger protein fusion in the pMal-c2 expression plasmid is under the control of the IPTG inducible tac promoter (NEB). Bacteria containing the MBP-zinc finger protein fusion plasmids are inoculated in to 2× YT medium containing 10 µM $ZnCl_2$, 0.02% glucose, plus 50 µg/ml ampicillin and shaken at 37° C. At mid-exponential growth IPTG is added to 0.3 mM and the cultures are allowed to shake. After 3 hours the bacteria are harvested by centrifugation, disrupted by sonication, and then insoluble material is removed by centrifugation. The MBP-zinc finger protein proteins are captured on an amylose-bound resin, washed extensively with buffer containing 20 mM Tris-HCl (pH 7.5), 200 mM NaCl, 5 mM DTT and 50 µM $ZnCl_2$, then eluted with maltose in essentially the same buffer (purification is based on a standard protocol from NEB). Purified proteins are quantitated and stored for biochemical analysis.

The biochemical properties of the purified proteins, e.g., $K_d$, can be characterized by any suitable assay. In one embodiment, $K_d$ is characterized via electrophoretic mobility shift assays ("EMSA") (Buratowski & Chodosh, in *Current Protocols in Molecular Biology* pp. 12.2.1–12.2.7 (Ausubel ed., 1996)).

V. Regulatory Domains

The chimeric zinc finger proteins made using the methods of the invention can optionally be associated with regulatory domains for modulation of gene expression. The chimeric zinc finger protein can be covalently or non-covalently associated with one or more regulatory domains, alternatively two or more regulatory domains, with the two or more domains being two copies of the same domain, or two different domains. The regulatory domains can be covalently linked to the chimeric zinc finger protein, e.g., via an amino acid linker, as part of a fusion protein. The zinc finger proteins can also be associated with a regulatory domain via a non-covalent dimerization domain, e.g., a leucine zipper, a STAT protein N terminal domain, or an FK506 binding protein (see, e.g., O'Shea, *Science* 254:539 (1991), Barahmand-Pour et al., *Curr. Top. Microbiol. Immunol.* 211: 121–128 (1996); Klemm et al., *Annu. Rev. Immunol.* 16:569–592 (1998); Klemm et al., *Annu. Rev. Immunol.* 16:569–592 (1998); Ho et al., *Nature* 382:822–826 (1996); and Pomeranz et al., *Biochem.* 37:965 (1998)). The regulatory domain can be associated with the chimeric zinc finger protein at any suitable position, including the C- or N-terminus of the chimeric zinc finger protein.

Common regulatory domains for addition to the chimeric zinc finger protein made using the methods of the invention include, e.g., heterologous DNA binding domains from transcription factors, effector domains from transcription factors (activators, repressors, co-activators, co-repressors), silencers, nuclear hormone receptors, oncogene transcription factors (e.g., myc, jun, fos, myb, max, mad, rel, ets, bcl, myb, mos family members etc.); and chromatin associated proteins and their modifiers (e.g., kinases, acetylases and deacetylases).

Transcription factor polypeptides from which one can obtain a regulatory domain include those that are involved in regulated and basal transcription. Such polypeptides include transcription factors, their effector domains, coactivators, silencers, nuclear hormone receptors (see, e.g., Goodrich et al., *Cell* 84:825–30 (1996) for a review of proteins and nucleic acid elements involved in transcription; transcription factors in general are reviewed in Barnes & Adcock, *Clin. Exp. Allergy* 25 Suppl. 2:46–9 (1995) and Roeder, *Methods Enzymol.* 273:165–71 (1996)). Databases dedicated to transcription factors are also known (see, e.g., *Science* 269:630 (1995)). Nuclear hormone receptor transcription factors are described in, for example, Rosen et al., *J. Med. Chem.* 38:4855–74 (1995). The C/EBP family of transcription factors are reviewed in Wedel et al., *Immunobiology* 193: 171–85 (1995). Coactivators and co-repressors that mediate transcription regulation by nuclear hormone receptors are reviewed in, for example, Meier, *Eur. J. Endocrinol.* 134 (2):158–9 (1996); Kaiser et al., *Trends Biochem. Sci.* 21:342–5 (1996); and Utley et al., *Nature* 394:498–502 (1998)). GATA transcription factors, which are involved in regulation of hematopoiesis, are described in, for example, Simon, *Nat. Genet.* 11:9–11 (1995); Weiss et al., *Exp. Hematol.* 23:99–107. TATA box binding protein (TBP) and its associated TAF polypeptides (which include TAF30, TAF55, TAF80, TAF110, TAF150, and TAF250) are described in Goodrich & Tjian, *Curr. Opin. Cell Biol.* 6:403–9 (1994) and Hurley, *Curr. Opin. Struct. Biol.* 6:69–75 (1996). The STAT family of transcription factors are reviewed in, for example, Barahmand-Pour et al., *Curr. Top. Microbiol. Immunol.* 211:121–8 (1996). Transcription factors involved in disease are reviewed in Aso et al., *J. Clin. Invest.* 97:1561–9 (1996).

In one embodiment, the KRAB repression domain from the human KOX-1 protein is used as a transcriptional repressor (Thiesen et al., *New Biologist* 2:363–374 (1990); Margolin et al., *Proc. Natl. Acad. Sci. U.S.A.* 91:4509–4513 (1994); Pengue et al., *Nucl. Acids Res.* 22:2908–2914 (1994); Witzgall et al., *Proc. Natl. Acad. Sci. U.S.A.* 91:4514–4518 (1994)). In another embodiment, KAP-1, a KRAB co-repressor, is used with KRAB (Friedman et al., *Genes Dev.* 10:2067–2078 (1996)). Alternatively, KAP-1 can be used alone with a zinc finger protein. Other preferred transcription factors and transcription factor domains that act as transcriptional repressors include MAD (see, e.g., Sommer et al., *J. Biol. Chem.* 273:6632–6642 (1998); Gupta et al., *Oncogene* 16:1149–1159 (1998); Queva et al., *Oncogene* 16:967–977 (1998); Larsson et al., *Oncogene* 15:737–748 (1997); Laherty et al., *Cell* 89:349–356 (1997); and Cultraro et al., *Mol Cell. Biol.* 17:2353–2359 (19977)); FKHR (forkhead in rhapdosarcoma gene; Ginsberg et al., *Cancer Res.* 15:3542–3546 (1998); Epstein et al., *Mol. Cell. Biol.* 18:4118–4130 (1998)); EGR-1 (early growth response gene product-1; Yan et al., *Proc. Natl. Acad Sci. U.S.A.* 95:8298–8303 (1998); and Liu et al., *Cancer Gene Ther.* 5:3–28 (1998)); the ets2 repressor factor repressor domain (ERD; Sgouras et al., *EMBO J.* 14:4781–4793 ((19095)); and the MAD smSIN3 interaction domain (SID; Ayer et al., *Mol. Cell. Biol.* 16:5772–5781 (1996)).

In one embodiment, the HSV VP16 activation domain is used as a transcriptional activator (see, e.g., Hagmann et al., *J. Virol.* 71:5952–5962 (1997)). Other preferred transcription factors that could supply activation domains include the VP64 activation domain (Seipel et al., *EMBO J.* 11:4961–4968 (1996)); nuclear hormone receptors (see, e.g., Torchia et al., *Curr. Opin. Cell. Biol.* 10:373–383 (1998)); the p65 subunit of nuclear factor kappa B (Bitko & Barik, *J. Virol.* 72:5610–5618 (1998) and Doyle & Hunt, *Neuroreport* 8:2937–2942 (1997)); and EGR-1 (early growth response gene product-1; Yan et al., *Proc. Natl. Acad. Sci. U.S.A.* 95:8298–8303 (1998); and Liu et al., *Cancer Gene Ther.* 5:3–28 (1998)).

Kinases, phosphatases, and other proteins that modify polypeptides involved in gene regulation are also useful as regulatory domains for chimeric zinc finger proteins. Such modifiers are often involved in switching on or off transcription mediated by, for example, hormones. Kinases involved in transcription regulation are reviewed in Davis, *Mol. Reprod. Dev.* 42:459–67 (1995), Jackson et al., *Adv. Second Messenger Phosphoprotein Res.* 28:279-86 (1993), and Boulikas, *Crit. Rev. Eukaryot. Gene Expr.* 5:1–77 (1995), while phosphatases are reviewed in, for example, Schonthal & Semin, *Cancer Biol.* 6:239–48 (1995). Nuclear tyrosine kinases are described in Wang, *Trends Biochem. Sci.* 19:373–6 (1994).

As described, useful domains can also be obtained from the gene products of oncogenes (e.g., myc, jun, fos, myb, max, mad, rel, ets, bcl, myb, mos family members) and their associated factors and modifiers. Oncogenes are described in, for example, Cooper, *Oncogenes*, 2nd ed., The Jones and Bartlett Series in Biology, Boston, Mass., Jones and Bartlett Publishers, 1995. The ets transcription factors are reviewed in Waslylk et al., *Eur. J. Biochem.* 211:7–18 (1993) and Crepieux et al., *Crit. Rev. Oncog.* 5:615–38 (1994). Myc oncogenes are reviewed in, for example, Ryan et al., *Biochem. J.* 314:713–21 (1996). The jun and fos transcription factors are described in, for example, *The Fos and Jun Families of Transcription Factors*, Angel & Herrlich, eds. (1994). The max oncogene is reviewed in Hurlin et al., *Cold Spring Harb. Symp. Quant. Biol.* 59:109–16. The myb gene family is reviewed in Kanei-Ishii et al., *Curr. Top. Microbiol. Immunol.* 211:89–98 (1996). The mos family is reviewed in Yew et al., *Curr. Opin. Genet. Dev.* 3:19–25 (1993).

In another embodiment, histone acetyltransferase is used as a transcriptional activator (see, e.g., Jin & Scotto, *Mol. Cell. Biol.* 18:4377–4384 (1998); Wolffe, *Science* 272:371–372 (1996); Taunton et al., *Science* 272:408–411 (1996); and Hassig et al., *Proc. Natl. Acad Sci. U.S.A.* 95:3519–3524 (1998)). In another embodiment, histone deacetylase is used as a transcriptional repressor (see, e.g., Jin & Scotto, *Mol. Cell. Biol.* 18:4377–4384 (1998); Syntichaki & Thireos, *J. Biol. Chem.* 273:24414–24419 (1998); Sakaguchi et al., *Genes Dev.* 12:2831–2841 (1998); and Martinez et al., *J. Biol. Chem.* 273:23781–23785 (1998)).

In addition to regulatory domains, often the chimeric zinc finger protein is expressed as a fusion protein such as maltose binding protein ("MBP"), glutathione S transferase (GST), hexahistidine, c-myc, and the FLAG epitope, for ease of purification, monitoring expression, or monitoring cellular and subcellular localization.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Methods

Plasmid construction. Zinc finger expression plasmids used in transfection studies were constructed by PCR amplification of DNA segments encoding the desired fingers of the Zif268 peptide and/or the NRE peptide. These DNA segments were inserted into the HindIII and BamHI sites of pCS, which had been constructed by subcloning an oligonucleotide duplex 5'-AGCTACCATGGCCAAGGAAAC-CGCAGCTGCCAAAT TCGAAAGACAGCATATGGAT-TCTAAGCTTCGCGGATCCT-3' (SEQ ID NO: 1) 5'-CTAGAGGATCCGCGAAGCTTAGAATC-CATATGCTGTCT TTCGAATTTGGCAGCTGCG-GTTTCCTTGGCCATGGT-3') (SEQ ID NO: 2) into the HindIII and XbaI sites of pcDNA3 (Invitrogen). These expression plasmids were designed to produce zinc finger peptides with both an S-peptide tag (Kim & Raines, *Protein Sci.* 2:348–356(1993); Kim & Raines, i. 219:165–166 (1995)) and a nuclear localization signal from SV40 large T-antigen (Kalderon et al., *Cell* 39:499–509 (1984)) at their N-terminus. Reporter plasmid were constructed by site-directed mutagenesis using the QuikChange™ kit (Stratagene). Construction of the template plasmid (pGL3-TATA/Inr) for the mutagenesis was described previously (Kim & Pabo, *J. Biol. Chem.* 272:29795–29800 (1997)). The DNA sequences of all constructs were confirmed by dideoxy sequencing.

Protein production and purification. The DNA segments encoding the Zif268, NRE, and 268//NRE peptides were amplified by PCR and subcloned into pGEX-6P-3 (Pharmacia). The zinc finger proteins were expressed in E. coli as fusions with glutathione S-transferase (GST) and were purified using affinity chromatography according to the manufacturer's protocol. These constructs did not have an S-peptide tag or an SV40 nuclear localization signal. GST was subsequently removed by digestion with PreScission™ Protease (Pharmacia). Protein concentrations were estimated by using SDS-polyacrylamide gel electrophoresis with bovine serum albumin as a standard (Pomerantz et al., *Science* 267:93–96 (1995)). Concentrations of active zinc finger proteins were determined essentially as described (Rebar & Pabo, *Science* 263:671–673 (1994)). These two methods gave comparable results, indicating that almost all of the protein was active.

Gel shift assay. DNA binding reactions contained the appropriate zinc finger peptide and binding site(s) in a solution of 20 mM bis-Tris propane pH 7.0, 100 mM NaCl, 5 mM $MgCl_2$, 20 mM $ZnSO_4$, 10% glycerol, 0.1% Nonidet P40, 5 mM DTT, and 0.10 mg/mL bovine serum albumin in a total volume of 10 mL. All binding experiments were performed at room temperature. The DNA sequences of the binding sites follow: N site, 5'-TCTGC AAGGGTTCA GGCGACACCAACCAA-3' (SEQ ID NO: 3); Z site, 5'-GT-GTGTGTGTGATCT GCGTGGGCG GTAAG-3' (SEQ ID NO: 4); NZ site, 5'-TCTGC AAGGGTTCA GCGTGGGCG GTAAG-3' (SEQ ID NO: 5); N/Z site, 5'-TCTGC AAGGGTTCA G GCGTGGGCG GTAAG-3' (SEQ ID NO: 6); and N//Z site, 5'-TCTGC AAGGGTTCA GT GCGTGGGCG GTAAG-3' (SEQ ID NO: 7). In each case, the 9-bp recognition sequences are underlined. Labeled DNAs used in gel shift assays were prepared by Klenow extension or kinase reaction.

To determine dissociation constants, 3-fold serial dilutions of the Zif268 or NRE peptide were incubated with a labeled probe DNA (0.4–1.4 pM) at room temperature for 1 h, and then the reaction mixtures were subjected to gel electrophoresis. The radioactive signals were quantitated by phosphorimager analysis; apparent dissociation constants were determined as described (Rebar & Pabo, *Science* 263:671–673 (1994)).

On-rates and off-rates were also determined by gel shift assay. To initiate the binding reaction when determining on-rate constants, a labeled probe DNA (final concentration, ~0.4 pM) was added to the zinc finger peptide (final concentration, 5–10 pM) at room temperature, and aliquots were analyzed by gel electrophoresis at various time points (0–20 min). The fraction bound at time t was determined by phosphorimager analysis of the gels. The data were then fit (KaleidaGraph™ program (Synergy Software)) to the equation:

$$F = F_{final}[1 - \exp(-k_{obs} \times t)]$$

where F is the fraction bound at time t; $F_{final}$ is the calculated fraction bound at the completion of the reaction; and $k_{obs}$ is the rate constant (Hoopes et al., *J. Biol. Chem.* 267:11539–11547 (1992)). The on-rate constant was calculated from the equation:

$$k_{on} = (F_{final} \times k_{obs})/[P]$$

where [P] is the concentration of the zinc finger protein. Off-rate constants were determined essentially as described (Kim et al., *Proc. Natl. Acad. Sci.* USA 94:3616–3620 (1997)). Proteins (final concentration, 100 pM) were preincubated with a labeled probe DNA for 1 hour and then a large excess of unlabeled probe DNA (final concentration, 20 nM) was added. Aliquots were removed at various time points and analyzed by gel electrophoresis. The fraction of labeled site was normalized to the fraction found at the end of the 1 hour preincubation period. The natural log of the normalized fraction bound was plotted against time, and the off-rate was determined from the slope. All data points for fast on-rate and off-rate measurements were corrected for the electrophoresis dead time.

Competition binding studies. The 268//NRE peptide (final concentration, 5 pM) was first incubated for 1 hour with various amounts of a cold competitor DNA (0, 0.05, 0.5, 5, and 50 nM), and then the labeled N/Z site (6–8 pM) was added. Samples were analyzed by gel electrophoresis after 2, 24, 48, 96, 190, and 600 hours. Specificity ratios (Kdc/Kd) were calculated from the equation:

$$K_{dc}/K_d = \{[C]/[P]_t\} \times (F_o \times F)/(F_o - F)(1-F)$$

where $K_{dc}$ is the dissociation constant for binding to the competitor DNA; $K_d$ is the dissociation constant for binding to the intact chimeric site; [C] is the concentration of competitor DNA; $[P]_t$ is the total-concentration of the protein; $F_o$ is the fraction bound in the absence of the competitor DNA; and F is the fraction bound in the presence of the competitor DNA. This equation assumes that the concentration of free protein is significantly smaller than that of protein bound to DNA. This criterion should readily be satisfied since the Kd of the 268//NRE peptide at the N/Z site is 3.8 fM, and 5 pM of the fusion peptide was used in these competition experiments:

Competition experiments with salmon sperm DNA contained the 268//NRE or Zif268 peptide (200 pM), the labeled N/Z site, and a slight molar excess of unlabeled N/Z site. Various amounts of salmon sperm DNA were added, and samples were analyzed by gel electrophoresis after 2, 24, and 48 hours incubation. When calculating specificity ratios, it was assumed that each base in the salmon sperm DNA represents the beginning of a potential (nonspecific) binding site.

Transient cotransfection assay. The 293 cells were transfected by calcium phosphate precipitation with a glycerol shock as described (Cepek et al., *Genes Dev.* 10:2079–2088 (1996)). Transfection experiments typically used cells at 10–30% confluency in monolayer cultures (6-well plates), and the following plasmids were added: 0.2 mg of the empty expression plasmid (pCS) or of expression plasmids encoding zinc finger peptides; 0.2 mg of a reporter plasmid; 1 mg of activator plasmid (GAL4-VP16); 0.1 mg of β-galactosidase expression plasmid (pCMVb; Clontech); and 2.5 mg of carrier plasmid (pUC19). The luciferase and β-galactosidase activities in the transfected cells were measured as described (Kim et al., *Proc. Natl. Acad. Sci.* USA 94:3616–3620 (1997); Kim & Pabo, *J. Biol. Chem.* 272:29795–29800 (1997)). All the zinc finger peptides expressed in 293 cells were quantitated by using the S.Tag™ Rapid Assay kit (Novagen) (Kim & Raines, *Protein Sci.* 2:348–356(1993); Kim & Raines, *Anal. Biochem.* 219:165–166 (1995)).

RESULTS

Structure-based design of poly-zinc finger-peptides. The design strategy involved linking two three-finger peptides, using longer (noncanonical) linkers at the junction to avoid introducing any strain. To further reduce any risk of interference or collision between the fingers, the linkers were designed so they could accommodate composite binding sites with one or two additional base pairs inserted between the individual 9-bp binding sites. Studies reported in this paper used the three-finger Zif268 peptide (which recognizes the site 5'-GCG TGG GCG-3'; SEQ ID NO: 8) and a three-finger "NRE" peptide (a Zif268 variant previously selected via phage display) that binds tightly and specifically to part of a nuclear hormone response element (5'-AAG GGT TCA-3'; SEQ ID NO: 9) (Greisman & Pabo, Science 275:657–661 (1997)). The composite target site with one additional base pair at the center has the sequence 5'-AAG GGT TCA G GCG TGG GCG-3' (SEQ ID NO: 10) and is called the N/Z site (N denotes the binding site for the NRE peptide and Z the binding site for Zif268). The site with two additional base pairs at the center has the sequence 5'-AAG GGT TCA GT GCG TGG GCG-3' (SEQ ID NO: 11) and is called the N//Z site.

Structure-based design, with the Zif268 complex (Pavletich & Pabo, Science 252:809–817 (1991); Elrod-Erickson et al., Structure 4:1171–1180 (1996)) as a model, was used to determine the appropriate length of linkers for making poly-finger proteins that could recognize each binding site (see FIGS. 1 and 2). At the N/Z site, it appeared that having 8 residues between the Leu at the a-helical end of the first peptide and the Tyr residue at the first b-sheet of the next peptide would allow sufficient flexibility. A canonical "TGEKP" linker has 4 residues (i.e., Gly-Glu-Lys-Pro) in this region. At the N//Z site, it seemed reasonable to use 11 residues between the Leu and the Tyr (FIG. 1A). Each linker (FIG. 1A) contained sequences that naturally flank the N-terminus and C-terminus of the three-finger Zif268 peptide. To allow additional flexibility, a glycine was included in the shorter linker (which still is 4 residues longer than a canonical linker), and a Gly-Gly-Gly-Ser sequence was included in the longer linker (which is 7 residues longer than a canonical linker). Using a notation analogous to that for the binding sites, the fusion protein with the shorter linker is denoted as 268/NRE and the fusion protein with the longer linker is denoted as 268//NRE.

Figure 3:
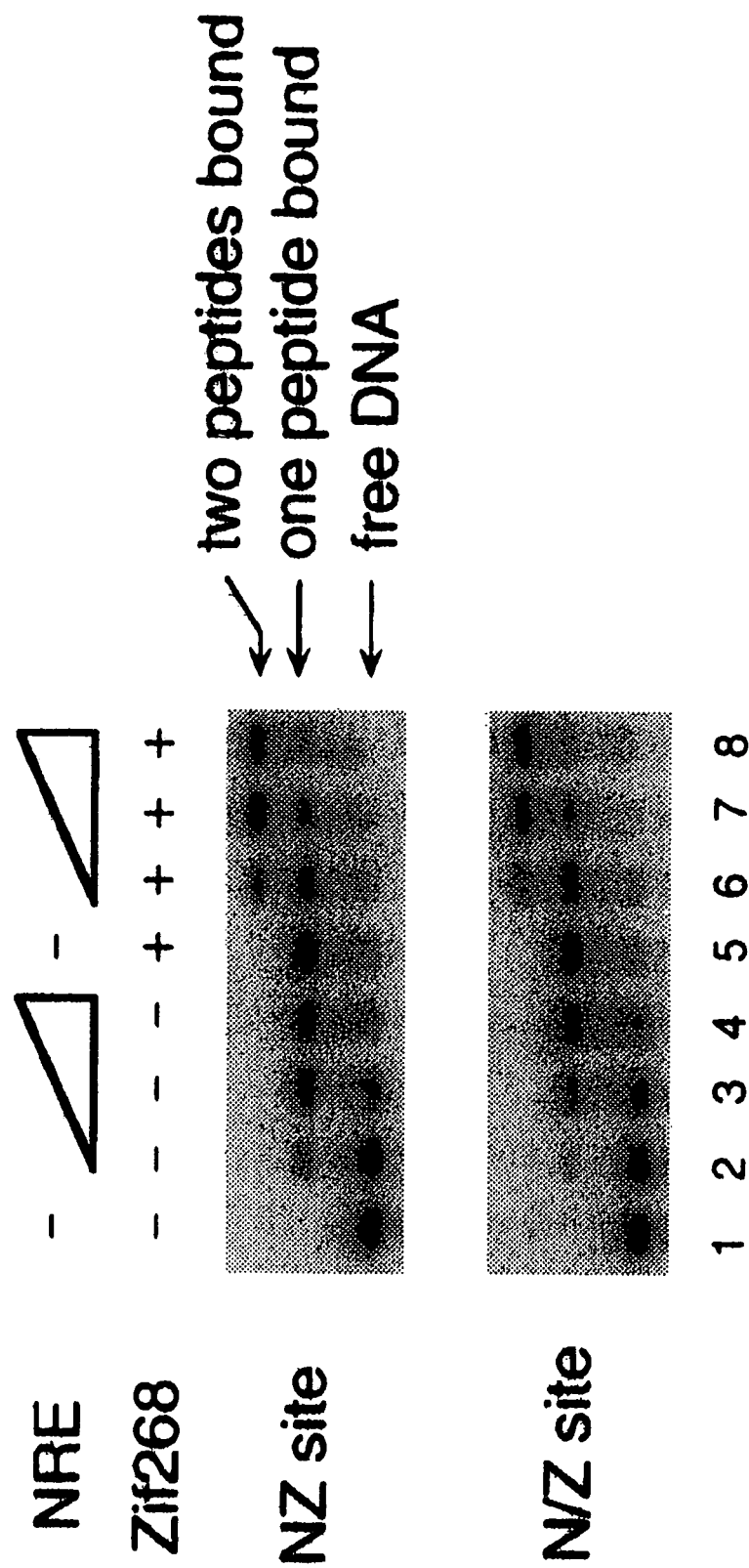
FIG. 3 depicts a gel shift assay various amounts (0, 0.01, 0.1, and 1 nM) of the NRE peptide were incubated for 1 hour with free binding sites (lanes 1–4) or binding sites preincubated with 0.1 nM of the Zif268 peptide for 0.5 hours (lanes 5–8). The positions of the free DNA and the protein-DNA complexes are indicated.

Gel shift assays to determine dissociation constants and half-lives of protein-DNA complexes. The Zif268, NRE, and 268//NRE zinc finger peptides were expressed and purified from E. coli, and used in several sets of gel shift experiments. A preliminary set of experiments was simply designed to determine whether two three-finger proteins could bind at adjacent 9-bp sites (any interference in binding of the unlinked peptides could reduce the affinity of a poly-finger protein for the composite sites). The first experiments used a DNA fragment (referred to as the NZ site) with the NRE- and Zif 268-binding sites directly juxtaposed (5'-AAG GGT TCA GCG TGG GCG-3'; SEQ ID NO: 12). Various amounts of the NRE peptide were incubated with labeled NZ site in the presence or absence of Zif268 (FIG. 3). It was determined that the three-finger NRE peptide actually binds slightly more tightly to the NZ site with prebound Zif268 than to the free site. The apparent dissociation constant ($K_d$) of the NRE peptide is 180 pM when it binds alone but 60 pM when Zif268 is prebound to the neighboring site. Similar results were obtained at the N/Z site. These experiments prove that there is no collision between peptides bound at adjacent sites and suggest that there may even be some modest cooperative effect. It appears that previous limits in the affinity of poly-finger proteins (Rebar (Ph.D. Thesis), Selection Studies of Zinc Finger-DNA Recognition, Massachusetts Institute of Technology (1997); Shi, (Ph.D. Thesis), Molecular Mechanisms of Zinc Finger Protein-Nucleic Acid Interactions, Johns Hopkins University (1995); Liu et al., Proc. Natl. Acad. Sci. USA 94:5525–5530 (1997)) were due to problems with linker design.

A second set of binding studies confirms the efficacy of the new linker design. Equilibrium titrations show that the 268//NRE peptide has significantly higher affinity for the composite sites than for the individual 9-bp sites (Table 1). The fusion protein binds to the isolated 9-bp sites with $K_d$s similar to those of the NRE peptide (180 pM) and the Zif268 peptide (14 pM) for their binding sites. In contrast, the 268//NRE fusion protein binds composite sites so tightly that dissociation constants are too small to readily be determined by protein titration. At least 0.4 pM of labeled probe DNA was needed in these gel shift experiments, making it difficult to accurately determine $K_d$ values of <1 pM. Given these technical difficulties, it was decided to measure the on-rate and off-rate for binding of the 268//NRE peptide and to use these rates to estimate the equilibrium binding constant (Table 1). Parallel studies with the three-finger peptides provided useful controls. On rates for the 268//NRE, NRE, and Zif268 peptides were fast and were close to the diffusion-controlled limit (108 to 109 M-1s-1) (von Hippel & Berg, I. 264:675–678 (1989)). The off rates showed amazing differences: The three-finger peptides have half-lives of <39 seconds, whereas the 268//NRE peptide has a half-life of 370 hours at the NZ site. Control studies show that the 268//NRE peptide forms a much less stable complex-with a single 9-bp site (thus the half-life=150 seconds at the N site). Both the NRE fingers and the Zif268 fingers must bind their respective 9-bp subsites to form the extraordinarily stable complex observed with the 268//NRE peptide at the NZ site.

In all cases where parallel measurements could be performed, $K_d$ values calculated from the ratio of kinetic constants ($k_{off}/k_{on}$) were in good agreement with those determined from equilibrium studies (Table 1). This gave confidence in using the kinetic data to determine $K_d$s in cases where direct titration was impracticable. Calculations show that the 268//NRE peptide has femtomolar affinity for the composite binding sites, with a $K_d$ of 2.1×10–15 M (2.1 fM) at the NZ site, 3.7 fM at the N/Z site, and 3.0 fM at the N//Z site (the consistency of these three $K_d$s also is encouraging since it would be expected that the longer, flexible linker should readily accommodate any of these spacings). The data show that the new linker design is quite effective: the 268//NRE fusion peptide binds far more tightly (5,000–95,000 fold) to the composite site than to the individual 9-bp sites, and it binds far more tightly (6,000–90,000 fold) than either of the original three-finger peptides.

TABLE 1

Dissociation Constants and Rate Data

| Protein | Binding site | $K_d$, pM | $k_{on}$, $M^{-1}s^{-1}$ | $k_{off}$, $s^{-1}$ |
|---|---|---|---|---|
| 268//NRE | N | 190 ± 50 | 2.5 ± 0.4 × $10^7$ | 4.7 ± 2.9 × $10^{-3}$ |
| 268//NRE | Z | 10* | | |
| 268//NRE | NZ | <1.0† | 2.5 ± 0.2 × $10^8$ | 5.2 ± 0.9 × $10^{-7}$ |
| 268//NRE | N/Z | <1.0† | 2.5 ± 0.2 × $10^8$ | 9.2 ± 0.7 × $10^{-7}$ |
| 268//NRE | N//Z | <1.0† | 2.6 ± 0.6 × $10^8$ | 7.7 ± 1.3 × $10^{-7}$ |
| NRE | N/Z | 180 ± 43 | >7.3 × $10^7$ | >5.9 × $10^{-2}$ |
| Zif268 | NZ | 12 ± 3 | | |
| Zif268 | N/Z | 14 ± 4 | >7.0 × $10^8$ | 1.4 ± 0.4 × $10^{-2}$ |
| Zif268 | N//Z | 14 ± 1 | | |

All the constants were determined in at least two separate experiments, and the SEM is indicated.
*An exact $K_d$ value could not be determined because this complex gave a smeared band on the gels.
†As explained in the text, these $K_d$ values could not be measured directly. Estimating $K_d$ from the ratio $k_{off}/k_{on}$ gives values of 2.1 fM at the NZ site, 3.7 fM at the N/Z site and 3.0 fM at the N//Z site.

Figure 4A:
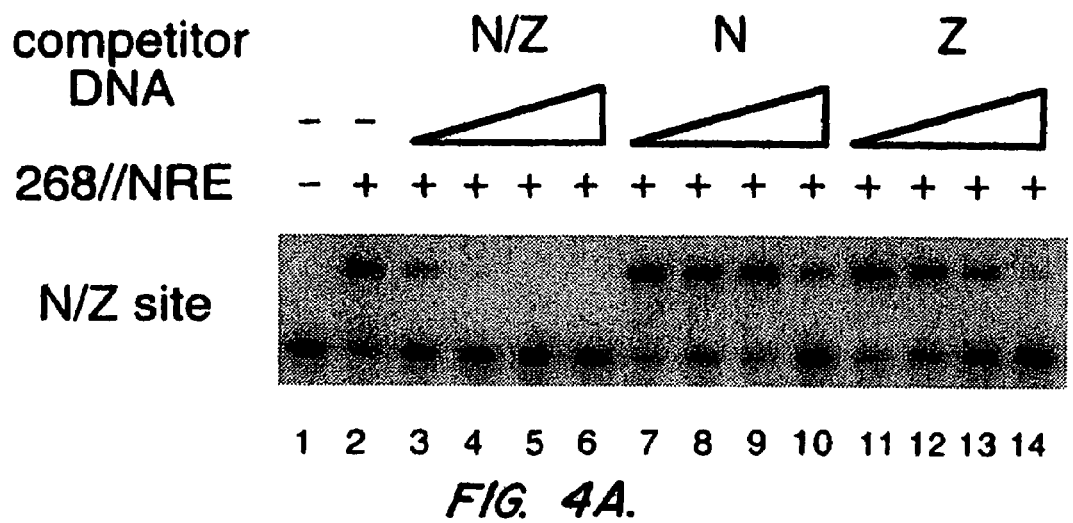
In FIG. 4A, the 268//NRE peptide (5 pM) was preincubated with various amounts (0.05, 0.5, 5 and 50 nM) of cold competitor DNAs (lanes 3–14) for 1 hour, and then a slight molar excess (over the peptide concentration) of the labeled N/Z site (608 pM) was added to the reaction mixture. Aliquots were analyzed by gel electrophoresis at various time points, and this gel shows the results after 600 hours of incubation time at room temperature.

Competition experiments were also used to further study the affinity and specificity of the six-finger 268//NRE peptide (FIG. 4A). One set of experiments directly tested how well the 9-bp N and Z sites could compete with the composite N/Z site for binding to the fusion peptide. In these experiments, various amounts of cold N or Z site were mixed with a limiting amount of the 268//NRE peptide. After 1 hour of incubation, a slightly molar excess (relative to the total amount of fusion protein) of labeled N/Z site was added. Under these conditions, about 70% of the labeled DNA is shifted in the absence of competitor DNA. Samples taken at various time points were analyzed by gel electrophoresis. Since the 268//NRE peptide concentration in this experiment (5 pM) is a few orders of magnitude higher than the peptide's dissociation constant for the N/Z site, almost all the peptide binds to the N/Z site when no competitor DNA is added. Any decrease in the amount of shifted N/Z site in the presence of competitor DNA reflects binding of the 268//NRE peptide to the competing site.

Equilibration in these experiments requires hundreds of hours, and the stability of the purified protein actually becomes a significant concern (the composite site is added last, and equilibration takes a long time since the fusion protein may encounter cold Z sites hundreds or thousands of times before it first encounters a labeled N/Z site). After pre-equilibration with high concentrations of cold N or Z site, it was determined that the fraction of N/Z label shifted-increases steadily with increasing incubation times of up to about 600 hours. After 600 hour of incubation, a significant fraction of the labeled N/Z site is shifted even in the presence of a 10,000-fold molar excess of cold N or Z site. Specificity ratios (calculated as described above) indicate that the 268//NRE peptide prefers the composite site over the N site by a factor of at least 3,800+1,600 and that the fusion peptide prefers the composite site over the Z site by a factor of at least 320+44. These experiments directly confirm the remarkable specificity of the six-finger peptide, but these values are only lower bounds on the specificity ratios. The protein sample loses some activity during the long incubation time required by these experiments (the activity of the free protein has a half-life of about 2 days under these conditions), and denatured protein will never have a chance to shift the labeled N/Z site.

Figure 4B:
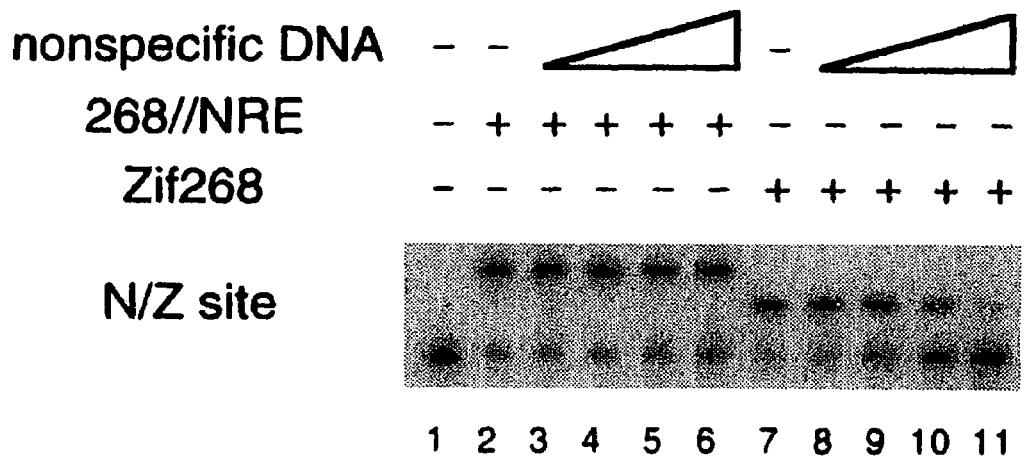
In FIG. 4B, the 268//NRE (lanes 2–6) or Zif268 peptide (lanes 7–11) was mixed with the labeled N/Z site, a slight molar excess (over the peptide concentration) of unlabeled N/Z site was added (so that 70% of the labeled site would be shifted in the absence of salmon sperm DNA), and various amounts of salmon sperm DNA (0, 0.1, 1, 10, and 100 μg/ml) were included. Samples were analyzed by gel electrophoresis after 24 hours of incubation.

Competition experiments with salmon sperm DNA were used to estimate the ratio of specific/nonspecific binding constants for the 268//NRE peptide (FIG. 4B). These experiments showed that the 268//NRE peptide discriminates very effectively against nonspecific DNA and indicate a specificity ratio ($K_{dns}/K_d$) of 8.8+1.5×10$^6$. Parallel experiments with the three-finger Zif268 peptide give a specificity ratio of 1.2+0.1×10$^5$. Previous studies, using calf thymus DNA as a competitor and slightly different conditions, had given a specificity ratio of 0.31×10$^5$ for the Zif268 peptide (Greisman & Pabo, Science 275:657–661 (1997)). Taken together, data on the affinity and specificity of the six-finger 268//NRE fusion peptide suggested that it might serve as a very effective repressor and certainly indicated that it would be an excellent candidate for further analysis in vivo.

Transient cotransfection studies in the 293 human cell line were used to see whether the new poly-finger peptides could effectively repress transcription from reporter genes. In a previous study, it had been shown that the Zif268 peptide could efficiently repress both basal and VP16-activated transcription when the Zif268 peptide bound to a site near the TATA box or the initiator element (Kim & Pabo, J. Biol. Chem. 272:29795–29800 (1997)). In this current study, a luciferase reporter and similar promoter constructs were used in which appropriate binding sites (Z, N, N/Z, and N//Z) were incorporated at comparable positions near the initiator element (FIG. 1B).

It was determined that the 268//NRE peptide gives 72-fold repression of VP16-activated transcription at a promoter containing the N/Z site and 47-fold repression at a promoter containing the N//Z site (FIGS. 5A–5D). The 268/NRE peptide gives 68-fold repression at the N/Z site. Clearly, these fusion peptides are very effective repressors at sites with the appropriate spacings. Parallel experiments with the three-finger peptides show repression but indicate that they are considerably less effective than the fusion peptides. Thus the NRE peptide gives 1.9-fold repression with an N site in the promoter; 1.8-fold repression with an N/Z site; 2.7-fold repression with an N//Z site; and no repression with an isolated Z site. The Zif268 peptide gives 13-fold repression from the Z promoter; 8.9-fold repression from the N/Z promoter; 15-fold repression from the N//Z promoter; and no repression with an isolated N site. Further experiments prove that covalent coupling is needed to achieve the much higher repression levels obtained with the fusion proteins at the N/Z site.

Thus co-expressing the Zif268 and NRE peptides as separate polypeptide chains (by including both expression plasmids in the cotransfection assays) gives only 8.5-fold repression at the N/Z site, a level comparable (within experimental error) to the 8.9-fold repression obtained at this site with the isolated Zif268 peptide. This is far less than the 68-fold and 72-fold repression that the 268/NRE and 268// NRE fusion proteins give at the N/Z site, and it is clear that these "synergistic" effects require covalent linkage.

It is noted that the additional fingers in the fusion peptides may have some modest repressive effects even in cases where only three of the fingers can bind specifically. Thus the six-finger peptides (268/NRE and 268//NRE) give 21 to 23-fold repression from the Z promoter. A similar (22-fold) repression level is obtained with the 268/NRE peptide at the N//Z site. Modeling suggests that the linker is too short to allow specific binding of all six fingers at this site. These repression levels are consistently somewhat higher than the level observed with the isolated Zif268 peptide at the Z site (13-fold repression). It seems possible (when the 268//NRE peptide binds to the Z site) that 1) the NRE fingers are free and yet sterically interfere with assembly of the transcription complex or that 2) the NRE fingers make weak nonspecific contacts with the DNA and thus slightly enhance the stability of the complex. Further studies indicate that all peptides are expressed at comparable levels.

The zinc finger peptides expressed in 293 cells had an S-peptide tag, and the amount of peptide was quantitated by using a ribonuclease assay after activating with S-protein (Kim & Raines, Protein Sci. 2:348–356(1993); Kim & Raines, Anal. Biochem. 219:165–166 (1995)). A conservative estimate indicates that the expression levels of the peptides in cells are significantly higher (at least 100 fold) than the dissociation constants of the three-finger peptides. Plasmids that would encode four- and five-finger variants of the 268/NRE and 268//NRE peptides were also constructed. These were tested in tissue culture transfection studies, and they typically gave repression levels intermediate between those obtained with the three-finger peptides and those obtained with the six-finger peptides (FIGS. 5A–5D).

What is claimed is:

1. A polynucleotide encoding a chimeric zinc finger protein that binds to adjacent target sites, the chimeric zinc finger protein comprising:
   (i) a first and a second DNA-binding domain polypeptide of the chimeric zinc finger protein, wherein at least one of the domains comprises an engineered zinc finger polypeptide, and wherein the first domain binds to a first target site and the second domain binds to a second target site, which target sites are adjacent; and
   (ii) a flexible linker that is six or more amino acids in length;
   wherein the first and second domains are fused with the flexible linker.

2. The polynucleotide of claim 1, wherein the adjacent target sites are separated by one nucleotide and the flexible linker is seven, eight, or nine amino acids in length.

3. The polynucleotide of claim 2, wherein the flexible linker has the amino acid sequence RQKDGERP (SEQ ID NO:14).

4. The polynucleotide of claim 1, wherein the adjacent target sites are separated by two nucleotides and the flexible linker is ten, eleven, or twelve amino acids in length.

5. The polynucleotide of claim 4, wherein the flexible linker has the amino acid sequence RQKDGGGSERP (SEQ ID NO:15).

6. The polynucleotide of claim 1, wherein the adjacent target sites are separated by three nucleotides and the flexible linker is twelve or more amino acids in length.

7. The polynucleotide of claim 1, wherein the first and the second domains are zinc finger polypeptides.

8. The polynucleotide of claim 7, wherein the zinc finger polypeptides are heterologous.

9. The polynucleotide of claim 7, wherein the chimeric zinc finger protein has femtomolar affinity for the adjacent target sites.

10. The polynucleotide of claim 9, wherein the chimeric zinc finger protein has about 2–4 femtomolar affinity for the adjacent target sites.

11. The polynucleotide of claim 1, wherein the chimeric zinc finger protein further comprises a regulatory domain polypeptide.

12. The polynucleotide of claim 1, wherein the first domain comprises a poly-finger zinc finger protein.

13. The polynucleotide of claim 12, wherein the second domain comprises a poly-finger zinc finger protein.

14. The polynucleotide of claim 11, wherein the regulatory domain is selected from the group consisting of a transcription activator domain and a transcription repressor domain.

15. The polynucleotide of claim 11, wherein the regulatory domain comprises an endonuclease.

16. The polynucleotide of claim 15, wherein the endonuclease comprises FokI.

17. A polynucleotide encoding a DNA-binding protein that binds to adjacent first and second target sites, wherein the adjacent target sites are separated by one nucleotide, the DNA-binding protein comprising first and second DNA-binding domains, wherein
    the first and second DNA-binding domains are zinc finger polypeptides (ZFPs) which do not occur together in the same arrangement in nature,
    the first ZFP binds to the first target site and the second ZFP binds to the second target site,
    each zinc finger polypeptide comprises a plurality of zinc fingers,
    each zinc finger comprises two conserved cysteine residues that are amino-terminal to two conserved histidine residues; and
    the first and second ZFPs are joined by an amino acid sequence of 9, 10 or 11 amino acids between the second conserved histidine residue of the carboxy-terminal zinc finger of the first ZFP and the first conserved cysteine residue of the amino-terminal zinc finger of the second ZFP.

18. The polynucleotide of claim 17, wherein the amino acid sequence joining the first and second ZFPs comprises the amino acid sequence RQKDGERP (SEQ ID NO:14).

19. A polynucleotide encoding a DNA-binding protein that binds to adjacent first and second target sites, wherein the adjacent target sites are separated by two nucleotides, the DNA-binding protein comprising first and second DNA-binding domains, wherein
the first and second DNA-binding domains are zinc finger polypeptides (ZFPs) which do not occur together in the same arrangement in nature,
the first ZFP binds to the first target site and the second ZFP binds to the second target site,
each zinc finger polypeptide comprises a plurality of zinc fingers,
each zinc finger comprises two conserved cysteine residues that are amino-terminal to two conserved histidine residues; and
the first and second ZFPs are joined by an amino acid sequence of 12, 13 or 14 amino acids between the second conserved histidine residue of the carboxy-terminal zinc finger of the first ZFP and the first conserved cysteine-residue of the amino-terminal zinc finger of the second ZFP.

20. A polynucleotide encoding a DNA-binding protein that binds to adjacent first and second target sites, the DNA-binding protein comprising
a regulatory domain; and
first and second DNA-binding domains, wherein
the first and second DNA-binding domains are zinc finger polypeptides (ZFPs) which do not occur together in the same arrangement in nature,
the first ZFP binds to the first target site and the second ZFP binds to the second target site,
each zinc finger polypeptide comprises a plurality of zinc fingers,
each zinc finger comprises two conserved cysteine residues that are amino-terminal to two conserved histidine residues; and
the first and second ZFPs are joined by an amino acid sequence comprising eight or more amino acids between the second conserved histidine residue of the carboxy-terminal zinc finger of the first ZFP and the first conserved cysteine residue of the amino-terminal zinc finger of the second ZFP.

21. The polynucleotide of claim 20, wherein the regulatory domain is selected from the group consisting of a transcription activator domain and a transcription repressor domain.

22. The polynucleotide of claim 20, wherein the regulatory domain comprises an endonuclease.

23. The polynucleotide of claim 22, wherein the endonuclease comprises FokI.

24. A polynucleotide encoding a DNA-binding protein that binds to first and second adjacent target sites, wherein the adjacent target sites are separated by one nucleotide, the DNA-binding protein comprising:
first and second zinc finger polypeptides (ZFPs), wherein each zinc finger polypeptide comprises a plurality of zinc fingers and each zinc finger comprises two conserved cysteine residues that are amino-terminal to two conserved histidine residues, and wherein the first ZFP binds to the first target site and the second ZFP binds to the second target site;
wherein the first and second ZFPs are joined by a sequence of 9, 10 or 11 amino acids between the second conserved histidine residue of the carboxy-terminal zinc finger of the first ZFP and the first conserved cysteine residue of the amino-terminal zinc finger of the second ZFP; and
further wherein the plurality of zinc fingers within each ZFP are joined by a sequence of seven amino acids between the second conserved histidine residue of a zinc finger and the first conserved cysteine residue of an adjacent zinc finger.

25. The polynucleotide of claim 24, wherein the amino acid sequence joining the first and second ZFPs comprises the amino acid sequence RQKDGERP (SEQ ID NO:14).

26. A polynucleotide-encoding a DNA-binding protein that binds to first and second adjacent target sites, wherein the adjacent target sites are separated by two nucleotides, the DNA-binding protein comprising:
first and second zinc finger polypeptides (ZFPs), wherein each zinc finger polypeptide comprises a plurality of zinc fingers and each zinc finger comprises two conserved cysteine residues that are amino-terminal to two conserved histidine residues, and wherein the first ZFP binds to the first target site and the second ZFP binds to the second target site;
wherein the first and second ZFPs are joined by a sequence of 12, 13 or 14 amino acids between the second conserved histidine residue of the carboxy-terminal zinc finger of the first ZFP and the first conserved cysteine residue of the amino-terminal zinc finger of the second ZFP; and
further wherein the plurality of zinc fingers within each ZFP are joined by a sequence of seven amino acids between the second conserved histidine residue of a zinc finger and the first conserved cysteine residue of an adjacent zinc finger.

27. A polynucleotide encoding a DNA-binding protein that binds to first and second adjacent target sites, the DNA-binding protein comprising:
a regulatory domain polypeptide; and
first and second zinc finger polypeptides (ZFPs), wherein each zinc finger polypeptide comprises a plurality of zinc fingers and each zinc finger comprises two conserved cysteine residues that are amino-terminal to two conserved histidine residues, and wherein the first ZFP binds to the first target site and the second ZFP binds to the second target site;
wherein the first and second ZFPs are joined by an amino acid sequence comprising eight or more amino acids between the second conserved histidine residue of the carboxy-terminal zinc finger of the first ZFP and the first conserved cysteine residue of the amino-terminal zinc finger of the second ZFP; and
further wherein the plurality of zinc fingers within each ZFP are joined by a sequence of seven amino acids between the second conserved histidine residue of a zinc finger and the first conserved cysteine residue of an adjacent zinc finger.

28. The polynucleotide of claim 27, wherein the regulatory domain is selected from the group consisting of a transcription activator domain and a transcription repressor domain.

29. The polynucleotide of claim 27, wherein the regulatory domain comprises an endonuclease.

30. The polynucleotide of claim 29, wherein the endonuclease comprises FokI.

* * * * *

UNITED STATES PATENT AND TRADEMARK OFFICE
CERTIFICATE OF CORRECTION

PATENT NO.        : 7,153,949 B2
APPLICATION NO.   : 11/110594
DATED             : December 26, 2006
INVENTOR(S)       : Jin-Soo Kim et al.

It is certified that error appears in the above-identified patent and that said Letters Patent is hereby corrected as shown below:

In the drawings: sheet 2 of 5, please replace FIGS 2A and 2B with the following:

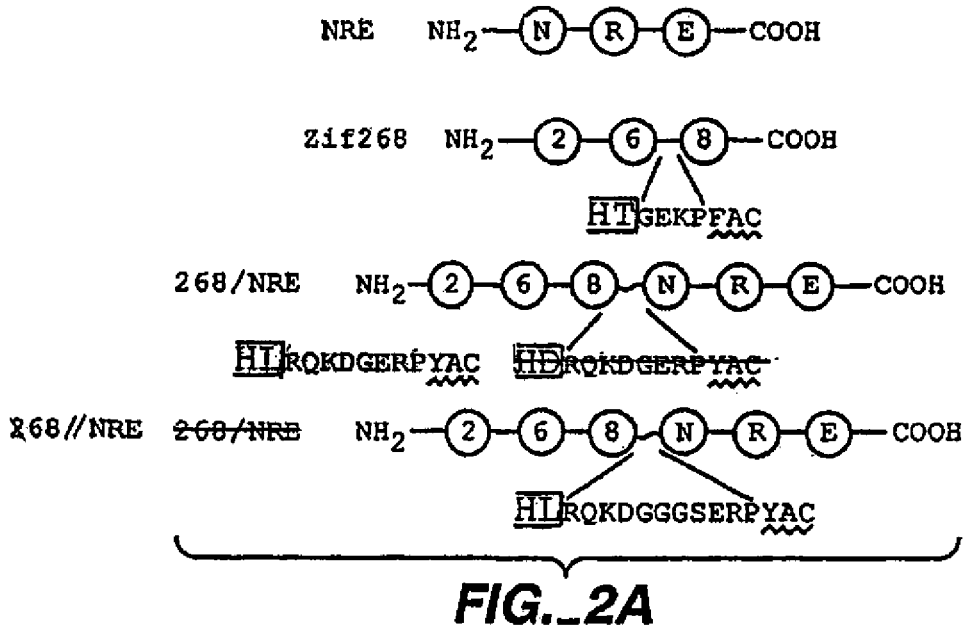

FIG._2A

UNITED STATES PATENT AND TRADEMARK OFFICE
CERTIFICATE OF CORRECTION

PATENT NO. : 7,153,949 B2  
APPLICATION NO. : 11/110594  
DATED : December 26, 2006  
INVENTOR(S) : Jin-Soo Kim et al.

Page 2 of 2

It is certified that error appears in the above-identified patent and that said Letters Patent is hereby corrected as shown below:

In the drawings:

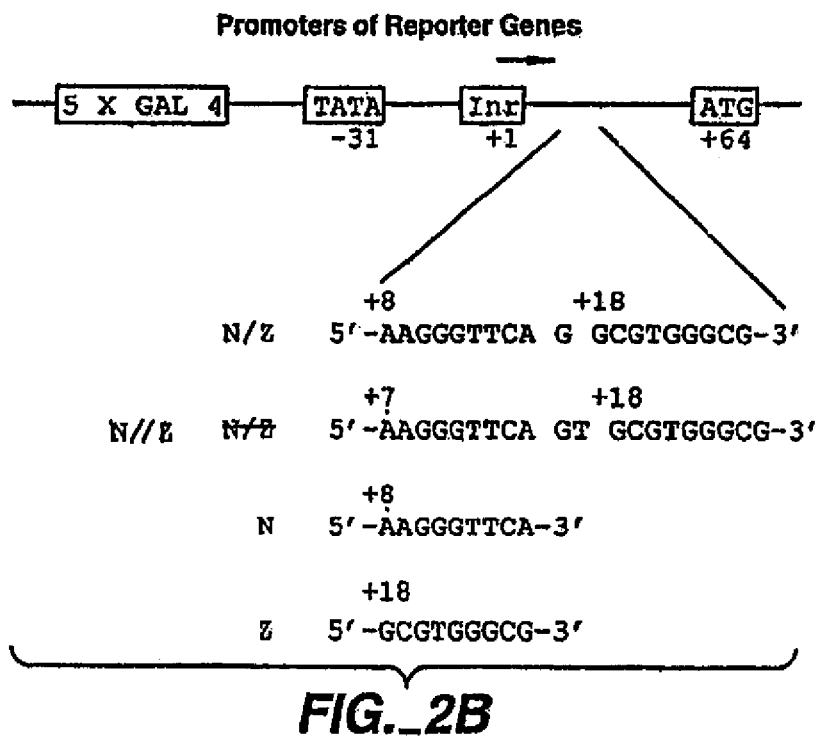

FIG._2B

Signed and Sealed this

First Day of December, 2009

David J. Kappos  
*Director of the United States Patent and Trademark Office*

SEQUENCE LISTING

<160> NUMBER OF SEQ ID NOS: 24

<210> SEQ ID NO 1
<211> LENGTH: 74
<212> TYPE: DNA
<213> ORGANISM: Artificial Sequence
<220> FEATURE:
<223> OTHER INFORMATION: Description of Artificial Sequence:
      oligonucleotide duplex

<400> SEQUENCE: 1

```
agctaccatg gccaaggaaa ccgcagctgc caaattcgaa agacagcata tggattctaa    60
gcttcgcgga tcct                                                      74
```

<210> SEQ ID NO 2
<211> LENGTH: 74
<212> TYPE: DNA
<213> ORGANISM: Artificial Sequence
<220> FEATURE:
<223> OTHER INFORMATION: Description of Artificial Sequence:
      oligonucleotide duplex

<400> SEQUENCE: 2

```
ctagaggatc cgcgaagctt agaatccata tgctgtcttt cgaatttggc agctgcggtt    60
tccttggcca tggt                                                      74
```

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence:N site zinc
      finger binding site
<220> FEATURE:
<221> NAME/KEY: protein_bind
<222> LOCATION: (6)..(14)
<223> OTHER INFORMATION: 9-bp N site zinc finger recognition sequence

<400> SEQUENCE: 3

```
tctgcaaggg ttcaggcgac accaaccaa                                      29
```

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence:Z site zinc
      finger binding site
<220> FEATURE:
<221> NAME/KEY: protein_bind
<222> LOCATION: (16)..(24)
<223> OTHER INFORMATION: 9-bp Z site zinc finger recognition sequence

<400> SEQUENCE: 4

```
gtgtgtgtgt gatctgcgtg ggcggtaag                                      29
```

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence:NZ site zinc
      finger binding site
<220> FEATURE:
<221> NAME/KEY: protein_bind
<222> LOCATION: (6)..(14)

```
<223> OTHER INFORMATION: 9-bp N site zinc finger recognition sequence
<220> FEATURE:
<221> NAME/KEY: protein_bind
<222> LOCATION: (15)..(23)
<223> OTHER INFORMATION: 9-bp Z site zinc finger recognition sequence

<400> SEQUENCE: 5
tctgcaaggg ttcagcgtgg gcggtaag                                        28

<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence:N/Z site
      zinc finger binding site
<220> FEATURE:
<221> NAME/KEY: protein_bind
<222> LOCATION: (6)..(14)
<223> OTHER INFORMATION: 9-bp N site zinc finger recognition sequence
<220> FEATURE:
<221> NAME/KEY: protein_bind
<222> LOCATION: (16)..(24)
<223> OTHER INFORMATION: 9-bp Z site zinc finger recognition sequence

<400> SEQUENCE: 6
tctgcaaggg ttcaggcgtg ggcggtaag                                       29

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:N//Z site
      zinc finger binding site
<220> FEATURE:
<221> NAME/KEY: protein_bind
<222> LOCATION: (6)..(14)
<223> OTHER INFORMATION: 9-bp N site zinc finger recognition sequence
<220> FEATURE:
<221> NAME/KEY: protein_bind
<222> LOCATION: (17)..(25)
<223> OTHER INFORMATION: 9-bp Z site zinc finger recognition sequence

<400> SEQUENCE: 7
tctgcaaggg ttcagtgcgt gggcggtaag                                      30

<210> SEQ ID NO 8
<211> LENGTH: 9
<212> TYPE: DNA
<213> ORGANISM: Artificial Sequence
<220> FEATURE:
<223> OTHER INFORMATION: Description of Artificial Sequence:three-finger
      Zif268 peptide recognition site

<400> SEQUENCE: 8 gcgtgggcg                                                              9

<210> SEQ ID NO 9
<211> LENGTH: 9
<212> TYPE: DNA
<213> ORGANISM: Artificial Sequence
<220> FEATURE:
<223> OTHER INFORMATION: Description of Artificial Sequence:three-finger
      NRE (nuclear hormone response element) peptide
      binding site

<400> SEQUENCE: 9 aagggttca                                                              9
```

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:N/Z site
      composite target site with one additional base
      pair at the center

<400> SEQUENCE: 10
aagggttcag gcgtgggcg                                                    19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:N//Z site
      composite tergat site with two additional base
      pairs at the center

<400> SEQUENCE: 11
aagggttcag tgcgtgggcg                                                   20

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:NZ site with
      NRE- and Zif268-binding sites directly juxtaposed

<400> SEQUENCE: 12
aagggttcag cgtgggcg                                                     18

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:canonical
      "TGEKP" linker

<400> SEQUENCE: 13

Thr Gly Glu Lys Pro
  1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:shorter
      flexible linker for fusion protein 268/NRE
      containing a glycine

<400> SEQUENCE: 14

Arg Gln Lys Asp Gly Glu Arg Pro
  1               5

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence:longer
      flexible linker for fusion protein 268//NRE containing a
      Gly-Gly-Gly-Ser sequence

```
<400> SEQUENCE: 15

Arg Gln Lys Asp Gly Gly Gly Ser Glu Arg Pro
  1               5                  10

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence:linker
      region in Zif268

<400> SEQUENCE: 16

His Thr Gly Glu Lys Pro Phe Ala Cys
  1               5

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence:linker
      region on 268/NRE

<400> SEQUENCE: 17

His Leu Arg Gln Lys Asp Gly Glu Arg Pro Tyr Ala Cys
  1               5                  10

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence:linker
      region in 268//NRE

<400> SEQUENCE: 18

His Leu Arg Gln Lys Asp Gly Gly Gly Ser Glu Arg Pro Tyr Ala Cys
  1               5                  10                  15

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:synthetic
      linker sequence

<400> SEQUENCE: 19

Gly Thr Gly Gln Lys Pro
  1               5

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence:synthetic
      linker sequence

<400> SEQUENCE: 20

Gly Glu Lys Pro
  1

<210> SEQ ID NO 21
<211> LENGTH: 25
```

```
<212> TYPE: PRT
<213> ORGANISM: Artificial Sequence
<220> FEATURE:
<223> OTHER INFORMATION: Description of Artificial Sequence:exemplary
      motif for C2H2 zinc finger protein
<220> FEATURE:
<221> NAME/KEY: MOD_RES
<222> LOCATION: (2)..(5)
<223> OTHER INFORMATION: Xaa = any amino acid
<220> FEATURE:
<221> NAME/KEY: MOD_RES
<222> LOCATION: (4)..(5)
<223> OTHER INFORMATION: Xaa may be present or absent
<220> FEATURE:
<221> NAME/KEY: MOD_RES
<222> LOCATION: (7)..(18)
<223> OTHER INFORMATION: Xaa = any amino acid
<220> FEATURE:
<221> NAME/KEY: MOD_RES
<222> LOCATION: (20)..(24)
<223> OTHER INFORMATION: Xaa = any amino acid
<220> FEATURE:
<221> NAME/KEY: MOD_RES
<222> LOCATION: (23)..(24)
<223> OTHER INFORMATION: Xaa may be present or absent

<400> SEQUENCE: 21

Cys Xaa Xaa Xaa Xaa Cys Xaa Xaa Xaa Xaa Xaa Xaa Xaa Xaa Xaa
 1               5                  10                  15

Xaa Xaa His Xaa Xaa Xaa Xaa Xaa His
            20                  25

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence:zinc finger
      target site with two overlapping D-able subsites
<220> FEATURE:
<221> NAME/KEY: modified_base
<222> LOCATION: (1)..(2)
<223> OTHER INFORMATION: n = g, a, c or t
<220> FEATURE:
<221> NAME/KEY: modified_base
<222> LOCATION: (5)
<223> OTHER INFORMATION: n = g, a, c or t
<220> FEATURE:
<221> NAME/KEY: modified_base
<222> LOCATION: (8)
<223> OTHER INFORMATION: n = g, a, c or t
<220> FEATURE:
<221> NAME/KEY: modified_base
<222> LOCATION: (9)
<223> OTHER INFORMATION: n = a, c or t; if g, then position 10 is g or t
<220> FEATURE:
<221> NAME/KEY: modified_base
<222> LOCATION: (10)
<223> OTHER INFORMATION: n = a or c; if position 9 is g, then n = g or t

<400> SEQUENCE: 22 nngkngknnn                                                            10

<210> SEQ ID NO 23
<211> LENGTH: 10
<212> TYPE: DNA
<213> ORGANISM: Artificial Sequence
<220> FEATURE:
<223> OTHER INFORMATION: Description of Artificial Sequence:zinc finger
      target site with three overlapping D-able subsites
<220> FEATURE:
<221> NAME/KEY: modified_base
<222> LOCATION: (1)..(2)
<223> OTHER INFORMATION: n = g, a, c or t
```

-continued

```
<220> FEATURE:
<221> NAME/KEY: modified_base
<222> LOCATION: (5)
<223> OTHER INFORMATION: n = g, a, c or t
<220> FEATURE:
<221> NAME/KEY: modified_base
<222> LOCATION: (8)
<223> OTHER INFORMATION: n = g, a, c or t

<400> SEQUENCE: 23 nngkngkngk                                                                10

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence:sequence
      included in longer linker to allow additional
      flexibility

<400> SEQUENCE: 24

Gly Gly Gly Ser
1
```